(12) United States Patent
Rylander et al.

(10) Patent No.: US 11,484,437 B2
(45) Date of Patent: Nov. 1, 2022

(54) SYSTEMS AND METHODS TO DECREASE INTRAUTERINE DEVICE EXPULSION AND PERFORATION

(71) Applicant: BOARD OF REGENTS, THE UNIVERSITY OF TEXAS SYSTEM, Austin, TX (US)

(72) Inventors: Christopher Rylander, Austin, TX (US); Christopher Idelson, Austin, TX (US); Marian Yvette Williams-Brown, Austin, TX (US); William Meador, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 544 days.

(21) Appl. No.: 16/485,957

(22) PCT Filed: Feb. 15, 2018

(86) PCT No.: PCT/US2018/018340
§ 371 (c)(1),
(2) Date: Aug. 14, 2019

(87) PCT Pub. No.: WO2018/152307
PCT Pub. Date: Aug. 23, 2018

(65) Prior Publication Data
US 2020/0054481 A1 Feb. 20, 2020

Related U.S. Application Data

(60) Provisional application No. 62/459,204, filed on Feb. 15, 2017.

(51) Int. Cl.
*A61F 6/18* (2006.01)
*A61B 17/04* (2006.01)
(Continued)

(52) U.S. Cl.
CPC ............ *A61F 6/18* (2013.01); *A61B 17/0469* (2013.01); *A61B 2017/00004* (2013.01);
(Continued)

(58) Field of Classification Search
CPC ...... A61B 17/0469; A61B 2017/00004; A61B 2017/06095; A61B 2017/06176;
(Continued)

(56) References Cited

U.S. PATENT DOCUMENTS

| 4,005,707 A | 2/1977 | Moulding, Jr. |
| 4,684,369 A | 8/1987 | Wildemeersch |

(Continued)

FOREIGN PATENT DOCUMENTS

| CN | 201283028 Y | 8/2009 |
| CN | 20164251 U | 11/2010 |
| CN | 102525723 | 7/2012 |

OTHER PUBLICATIONS

International Search Report and Written Opinion issued in International Application No. PCT/US2018/018340, dated Apr. 24, 2018.
(Continued)

*Primary Examiner* — Tuan V Nguyen
(74) *Attorney, Agent, or Firm* — Parker Highlander PLLC

(57) ABSTRACT

System and methods for inserting and securing an intrauterine device.

24 Claims, 29 Drawing Sheets

(51) Int. Cl.
*A61B 17/00* (2006.01)
*A61B 17/06* (2006.01)
*A61B 17/30* (2006.01)
*A61B 17/42* (2006.01)

(52) U.S. Cl.
CPC .............. *A61B 2017/06095* (2013.01); *A61B 2017/06176* (2013.01); *A61B 2017/306* (2013.01); *A61B 2017/4216* (2013.01)

(58) Field of Classification Search
CPC ....... A61B 2017/306; A61B 2017/4216; A61F 6/18; A61F 6/144
See application file for complete search history.

(56) References Cited

U.S. PATENT DOCUMENTS

| | | | |
|---|---|---|---|
| 4,708,134 A | | 11/1987 | Wildemeersch |
| 4,721,105 A | * | 1/1988 | Wildemeersch ........ A61F 6/144 128/840 |
| 4,949,732 A | * | 8/1990 | Spoon ...................... A61F 6/18 128/839 |
| 5,303,717 A | | 4/1994 | Wildemeersch |
| 5,433,218 A | | 7/1995 | Wildemeersch |
| 6,588,429 B1 | * | 7/2003 | Wildemeersch .......... A61F 6/18 128/830 |
| 6,742,520 B1 | | 6/2004 | Wildemeersch |
| 7,080,647 B2 | | 7/2006 | Wildemeersch |
| 2008/0058869 A1 | * | 3/2008 | Stopek ............. A61B 17/06066 606/228 |
| 2012/0318276 A1 | | 12/2012 | Wildemeersch |
| 2015/0359663 A1 | | 12/2015 | Wildemeersch |

OTHER PUBLICATIONS

Machine translation of CN 102525723, downloaded from https://patents.google.com/patent/CN102525723A/en?oq=CN+102525723 on Sep. 14, 2021.

Machine translation of CN 201283028Y, downloaded from https://patents.google.com/patent/CN201283028Y/en?oq=CN+201283028 on Sep. 14, 2021.

Machine translation of CN 201642510U, downloaded from https://patents.google.com/patent/CN201642510U/en?oq=CN+201642510+U on Sep. 14, 2021.

* cited by examiner

SYSTEMS AND METHODS TO DECREASE INTRAUTERINE DEVICE EXPULSION AND PERFORATION

CROSS-REFERENCE TO RELATED APPLICATIONS

This application is a national phase application under 35 U.S.C. § 371 of International Application No. PCT/US2018/018340, filed Feb. 15, 2018, which claims priority to U.S. Provisional Patent Application Ser. No. 62/459,204 filed Feb. 15, 2017, the entire contents of each of which are incorporated herein by reference.

GOVERNMENT SUPPORT CLAUSE

This invention was made with government support under grant no. IIP1745609 awarded by The National Science Foundation. The government has certain rights in the invention.

BACKGROUND INFORMATION

Intrauterine devices (IUDs) are long acting reversible contraceptives that are highly effective, with a 0.2-0.8% failure rate [6]. Many countries across the globe, including China and India, have greater proportional use of IUDs relative to other contraceptive options due to their superior effectiveness [39-41]. While scientific evidence strongly supports IUD contraceptive performance of both copper and hormone-releasing IUDs, (e.g.; Paragard and Mirena), certain shortcomings exist which affect accessibility, uptake, use, and satisfaction. In particular, IUD insertion during the postpartum (i.e.; post-placental or PP) period, has been shown to correlate to high expulsion rates, averaging 9-30 percent [4,8,9], compared to 3 percent for interval insertions (four or more weeks after birth). Thus, many clinicians do not provide PP IUD insertion, missing the crucial window of opportunity to provide this service when they are most accessible to patients.

Women who do receive PP IUD insertion may have an unnoticed expulsion, potentially resulting in unwanted pregnancy. Women who do notice an IUD expulsion often do not seek a replacement for several reasons including cost, accessibility to the physician or clinic, or inconvenience (especially while adapting to increased childcare responsibilities). Studies indicate clinician experience and insertion technique likely play a key role in expulsion rates due to difficulty of IUD deployment near the targeted upper fundal region, especially PP when the uterus is larger [4,9-13]. Uterine contractile forces and changing geometry during PP involution and menstrual cycles also heavily factor into the higher expulsion rates [4,9-13,15,16].

An uncommon problem of IUDs is perforation of the uterus; either primary (at the time of insertion) or secondary (4 or more weeks after insertion), reported as occurring once every 1000 insertions, and more common in postpartum and during lactation [4, 9, 42, 43].

In the United States, nearly half of the pregnancies are unintended. Effective contraception after child birth not only helps to reduce the rate of unintended pregnancies, it improves the health of both mothers and infants by increasing birth intervals [7]. However, despite the benefits of preventing unwanted pregnancies, issues regarding education, access, and cost are barriers of IUD use. Placement of the IUD after delivery has medical and personal advantages for women, and would also improve access as well as continuation rates.

However, expulsion rates of postpartum (PP) placement are, on average, 15-20% [8]. Data suggest IUD insertions taking place during the PP period are heavily correlated to increased expulsion rates as compared to interval insertions (e.g. four or more weeks after birth). Extensive systematic reviews comparing IUD insertion at different post-placenta time windows show notable differences between expulsion rates of insertions within 10 minutes of delivery (approximately 9 percent) compared to "delayed" PP insertions between 10 minutes and 48 hours (approximately 20 percent expulsion rate) [4, 9]. Immediate PP insertions still had higher expulsion rates when compared to interval insertions (approximately 3 percent). These and other studies indicate clinician experience and insertion technique likely play a key role in expulsion rates due to difficulty of IUD deployment in the upper fundal region, especially PP when the uterus is larger [4, 9-13]. An uncommon problem of IUDs is perforation of the uterus—either primary (at the time of insertion) or secondary (4 or more weeks after insertion), reported as occurring in every 1000-2500 insertions, and more common in postpartum and during lactation.

Though IUD insertion devices exist for standard interval insertion, very few are compatible for PP insertion, and they are not well adopted by clinicians [16, 17]. Most often, PP IUD insertion is accomplished without an inserter by the clinician either using their own hand or ring forceps. However, there does not appear to be a clear and consistent standard for the process, as clinician preference seems to vary by geographical area and specific training received.

There is presently a shortage of methods and devices that provide for secure placement of an IUD in the uterine cavity. Exemplary embodiments of the present disclosure address these shortcomings.

SUMMARY

Exemplary embodiments of the present disclosure include systems and methods for inserting and securing an IUD in the uterine cavity. In certain embodiments, the system comprises a barbed suture; an intrauterine device configured to couple to the barbed suture; and a needle. In particular embodiments, the suture may not be barbed. In particular embodiments, the needle is configured to direct the barbed suture into a uterine cavity wall, and the barbed suture comprises a first end and a second end. In specific embodiments, the barbed suture is configured to be removed from the uterine cavity wall. Then the first end of the barbed suture is pulled in a direction away from the uterine cavity wall; and the barbed suture is configured to remain in the uterine cavity wall when the second end of the barbed suture is pulled in a direction away from the uterine cavity wall.

Certain embodiments further comprise a suction device configured to create a vacuum on a target region of the uterine cavity wall. In particular embodiments, the suction device comprises a first end, a second end, an inner conduit, and a plunger disposed within the inner conduit. In some embodiments, the suction device comprises a first channel configured to guide the needle and the barbed suture toward the uterine cavity wall. In specific embodiments, the suction device comprises a second channel configured to guide the needle and the barbed suture away from the uterine cavity wall. In certain embodiments, the first channel comprises a first curved portion proximal to the first end, wherein the curved portion is configured to direct the needle and the barbed suture d the inner conduit. In particular embodiments, the second channel comprises a second curved portion configured to direct the needle and the barbed sutured from the inner conduit toward the second end of the suction device. In some embodiments, the first curved portion is configured to direct the needle to penetrate into the uterine cavity wall at a first location; and the second curved portion is configured receive the needle from the uterine cavity wall at a second location.

In specific embodiments, the needle is flexible. In certain embodiments, the needle is retractable. In particular embodiments, the intrauterine device is a frameless intrauterine device. In some embodiments, the intrauterine device is a commercially available T-shaped IUD such as those available from Mirena, Skyla, Kyleena, Liletta, or Paragard. In specific embodiments, the intrauterine device comprises an aperture configured to receive the barbed suture.

In certain embodiments, the barbed suture is biodegradable. In particular embodiments, the barbed suture is configured to degrade and release the intrauterine device in a period of time between one month and one year after the barbed suture is coupled to the intrauterine device and inserted in a uterine cavity wall. In some embodiments, the barbed suture is configured to degrade and release the intrauterine device in a period of time between six weeks and six months after the barbed suture is coupled to the intrauterine device and inserted in a uterine cavity wall.

Certain embodiments further comprise an insertion device configured to insert the suture in a target region of the uterine cavity wall. In particular embodiments, the needle is configured to guide the suture into the uterine cavity wall creating a loop configuration. In some embodiments, the needle is first extended and then retracted from the insertion device to guide the suture into the uterine cavity wall.

Certain embodiments include a method of inserting an intrauterine device in a uterine cavity, the method comprising: coupling an intrauterine device to a barbed suture, and inserting the barbed suture into a uterine cavity wall to secure the intrauterine device in the uterine cavity, wherein inserting the barbed suture into the uterine wall comprises directing the barbed suture into a first location of the uterine cavity wall, and directing the barbed suture out of a second location of the uterine cavity wall.

Particular embodiments further comprise creating a vacuum on a target region of the uterine wall cavil comprising the first location and the second location of the uterine cavity wall. In some embodiments, creating a vacuum on the target region of the uterine cavity wall comprises: placing a suction device proximal to the target region of the uterine cavity wall, wherein the suction device comprises a first end, a second end, an inner conduit, and a plunger disposed within the inner conduit; engaging the first end of the suction device with the uterine cavity wall; positioning the first end of the suction device around the target region of the uterine cavity wall; and moving the plunger away from the first end of the suction device and toward the second end of the suction device.

In some embodiments, the uterine cavity wall is a fundus. Specific embodiments further comprise positioning the barbed suture such that the barbed suture forms a loop in the uterine cavity. In particular embodiments, the barbed suture comprises a first end and a second end, and wherein the first end and the second end are distal from the uterine cavity wall. Certain embodiments, further comprise removing the barbed suture from the uterine cavity wall by pulling the first end of the barbed suture in a direction away from the uterine cavity wall. In some embodiments, the barbed suture is biodegradable.

In specific embodiments, the barbed suture degrades and releases the intrauterine device in a period of time between one month and one year after the barbed suture is coupled to the intrauterine device and inserted in a uterine cavity wall. In some embodiments, the barbed suture degrades and releases the intrauterine device in a period of time between six weeks and six months after the barbed suture is coupled to the intrauterine device and inserted in a uterine cavity wall.

As used herein, the term "intrauterine device" and "IUD" are used to refer to contraceptive devices placed in the uterine cavity.

In the present disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "approximately, "about" or "substantially" mean, in general, the stated value plus or minus 10%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed. In addition, a method that recites multiple steps does not require the steps be performed in the order recited.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF ILLUSTRATIVE EMBODIMENTS

Figure 1:
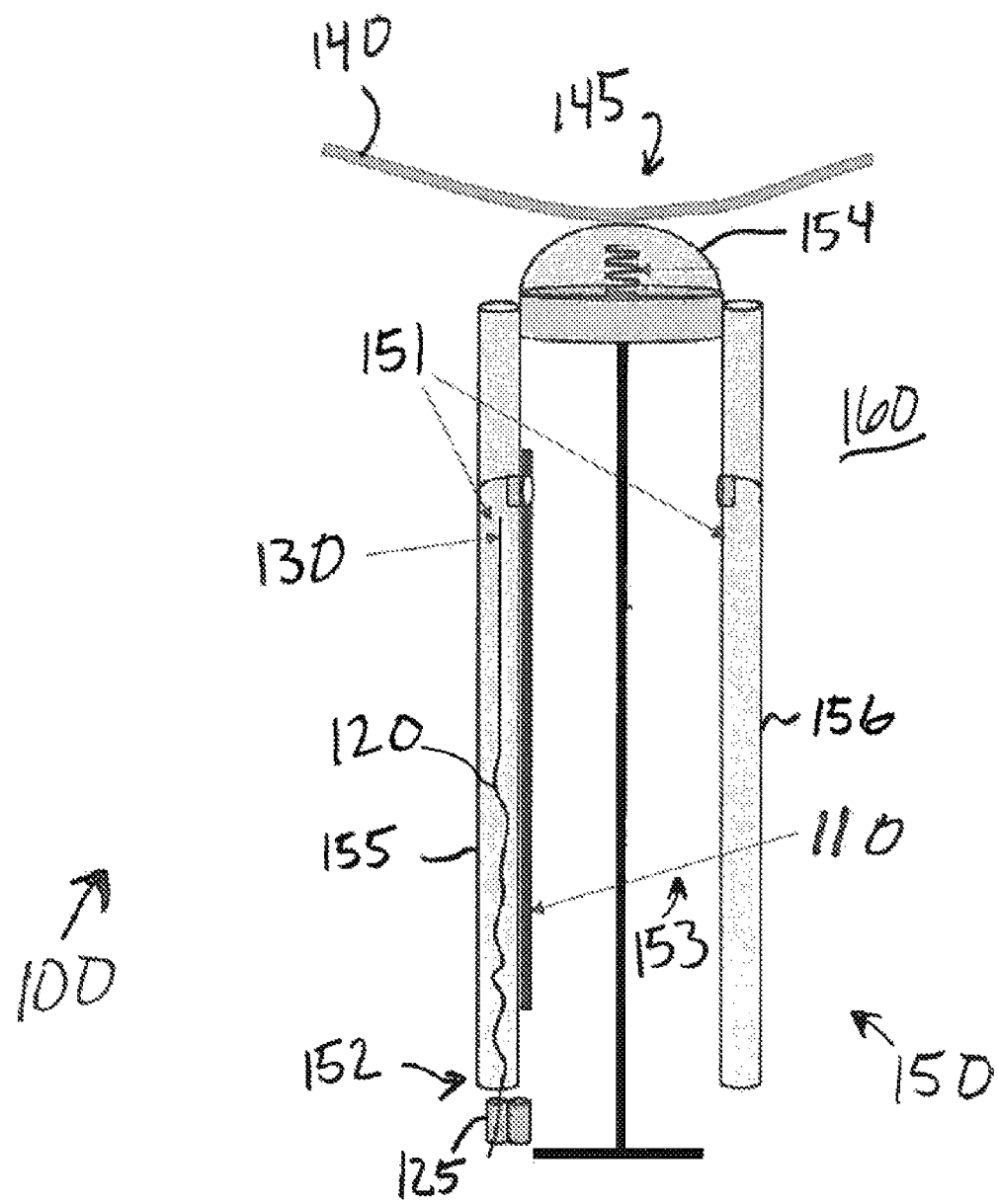
FIGS. 1-5 illustrate an exemplary embodiment of a system and method of securing an IUD as disclosed herein.
Figure 2:
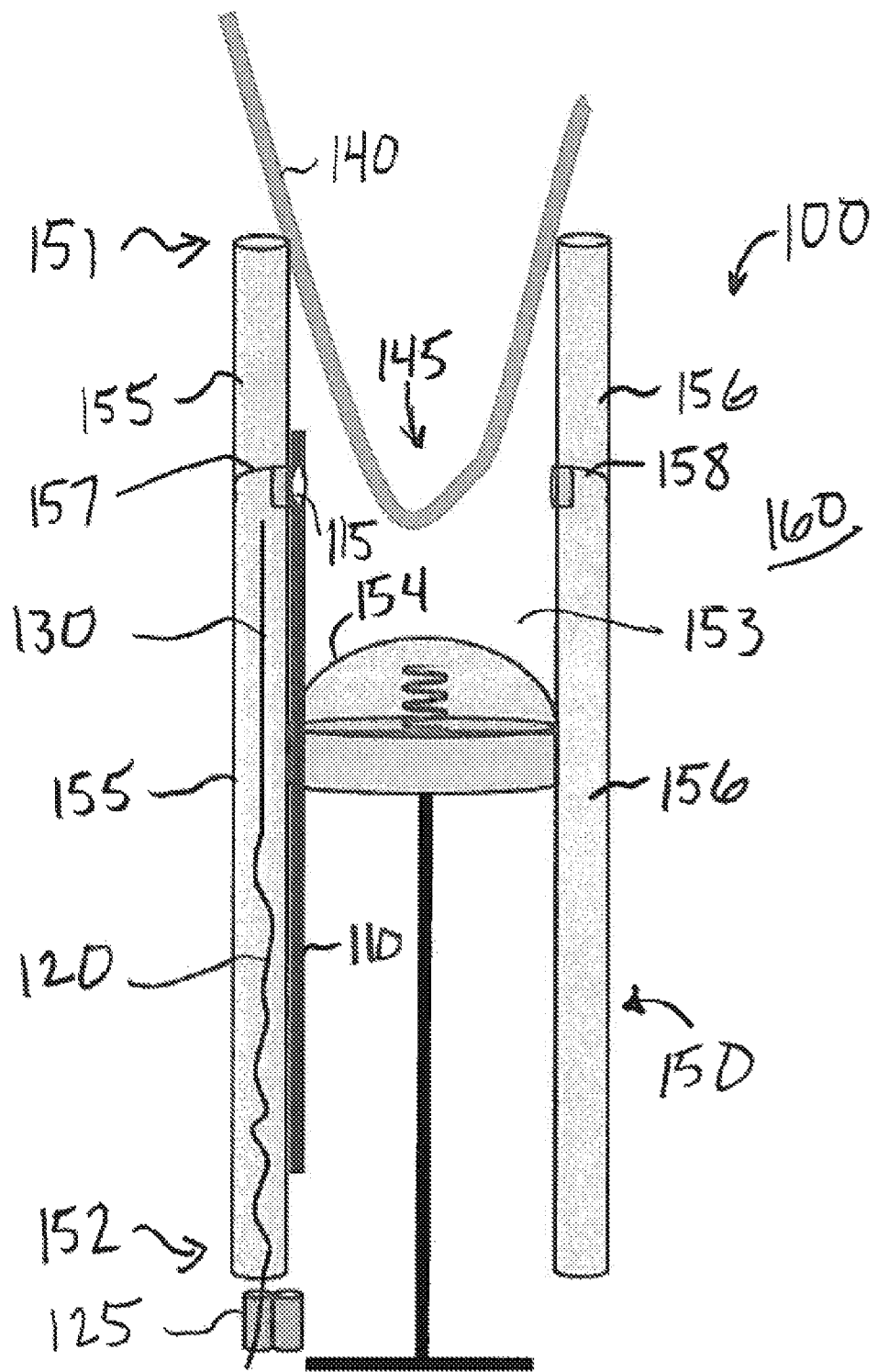
Figure 3:
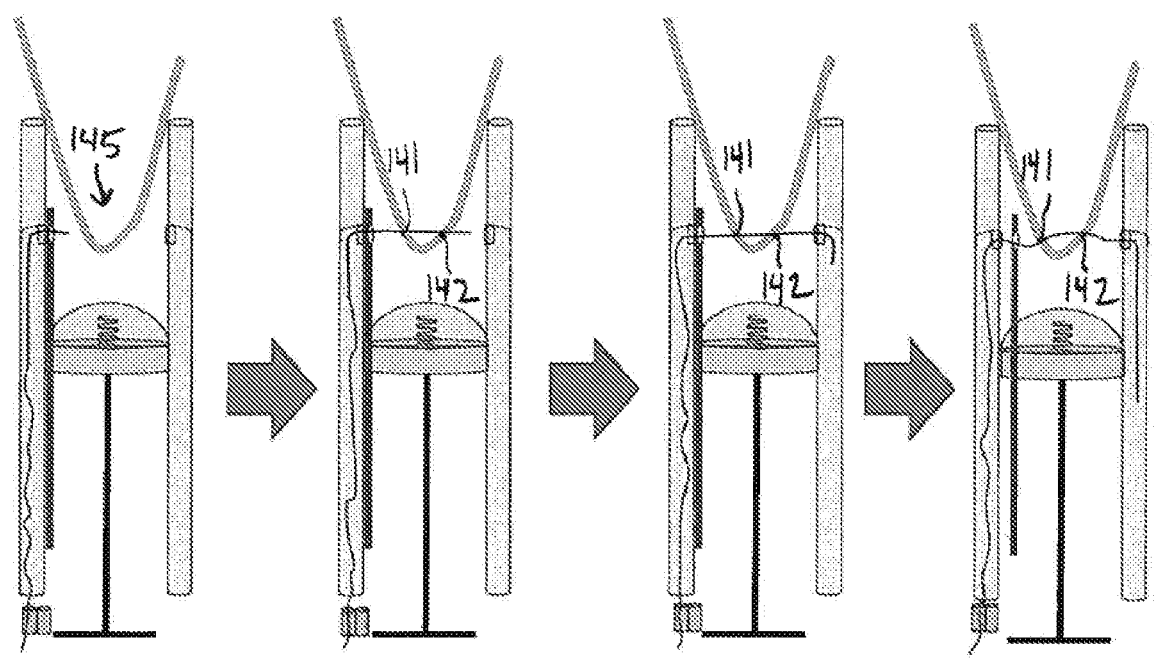
Figure 4:
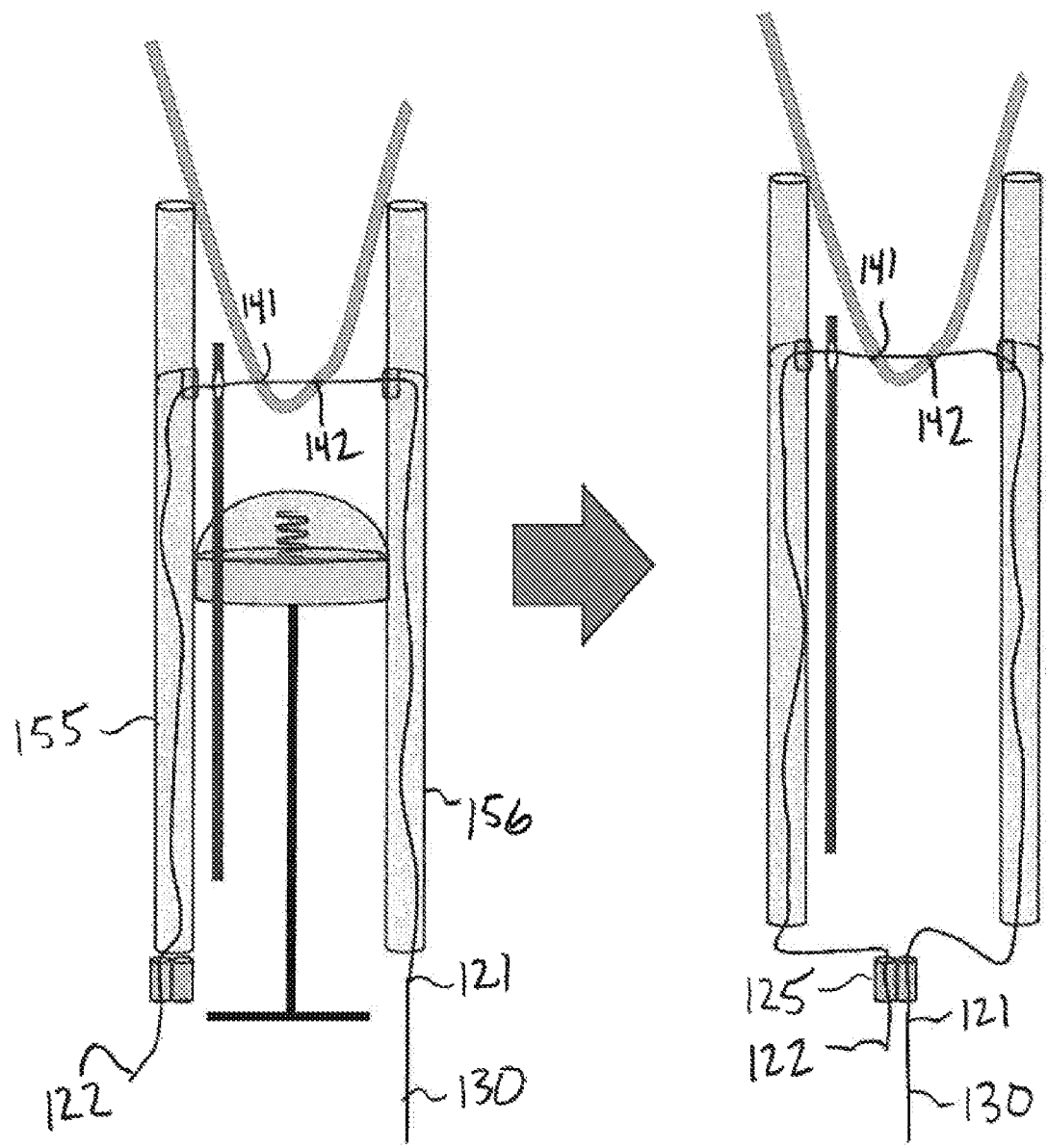
Figure 5:
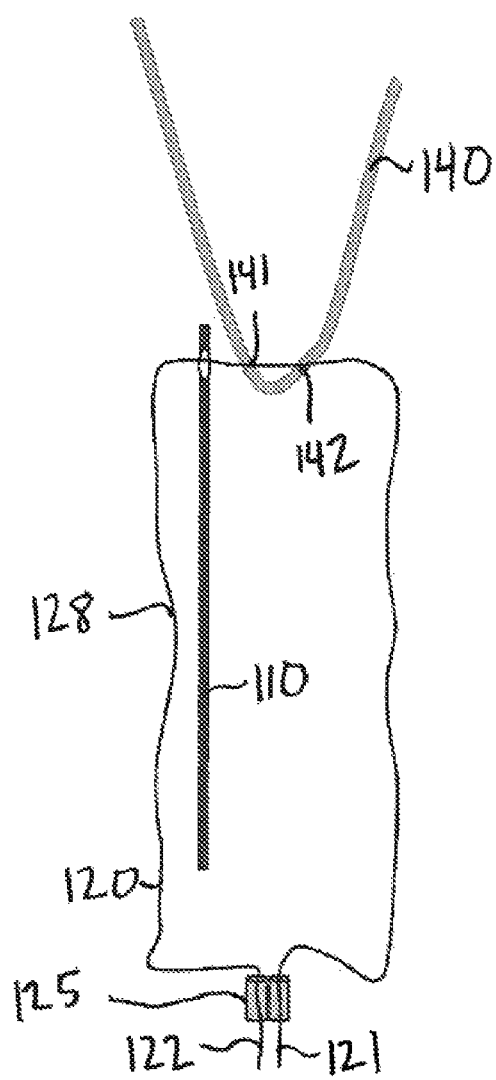

Referring initially to FIGS. 1-5, an exemplary embodiment of a system 100 comprises an intrauterine device (IUD) 110, a suture 120, and a needle 130. The embodiment shown in FIG. 1 also comprises a suction device 150 configured to create a vacuum on a target region 145 of a uterine cavity wall 140. In particular embodiments, suture 120 may be configured as a barbed suture, and uterine cavity wall 140 may be the fundus. In other embodiments, suture 120 may not be a barbed suture. In the embodiment shown in FIGS. 1-5, suction device 150 comprises a first end 151, a second end 152, an inner conduit 153 and a plunger 154 disposed within inner conduit 153.

FIGS. 1-5 depict system 100 at various stages of inserting and securing IUD 100 in a uterine cavity 160. It is understood that the method of inserting and securing IUD 100 shown in FIGS. 1-5 is merely one exemplary embodiment, and other methods of insertion and securement of IUD 100 may be implemented in other embodiments.

As shown in FIGS. 1-5, suction device 150 has been inserted into uterine cavity 160 so that first end 151 of suction device 150 is proximal to target region 145 of uterine cavity wall 140. Suction device 150 can then be located such that first end 151 of suction is positioned around target region 145. With suction device 150 positioned accordingly, plunger 154 can be moved away from first end 151 and toward second end 152. This creates a suction effect and provides a vacuum in inner conduit 153 between plunger 154 and target region 145 of uterine cavity wall 140. Target region 145 is drawn into inner conduit 153 as a result of the vacuum.

With target region 145 located in inner conduit 153, needle 130 and suture 120 can be directed through a coupling mechanism 125 and a first channel 155 that is adjacent inner conduit 153. Needle 130 can then be directed through IUD 110 and into inner conduit 153, such that needle 130 is directed into a first location 141 of uterine cavity wall 140 and directed out of a second location 142 of uterine cavity wall 140. With suture 120 coupled to needle 130, suture 120 is thereby inserted into uterine cavity wall 140 (e.g. the myometrium or muscle layer of wall 140) by entering at first location 141 and exiting at second location 142. In exemplary embodiments, suture 120 (or other anchoring mechanisms disclosed herein) may be inserted into a target region of a uterine wall without perforating the entire thickness of the wall.

In the embodiment shown, needle 130 and suture 120 can then be directed into a second channel 156 that is adjacent inner conduit 153 of suction device 150. Needle 130 and suture 120 can then be directed toward second end 152 of suction device 150, and plunger 154 removed from inner conduit 153. Suction device 150 can also then be removed from uterine cavity 160. In particular embodiments, suction device 150 can be configured to release suture 120 (e.g. by including two halves that can be separated) before removal from uterine cavity 160.

First and second channels 155 and 156 may respectively comprise curved portions 157 and 158 to assist in guiding needle 130 in the desired manner. In addition, IUD 110 may comprise an aperture 115 configured to receive needle 130 and barbed suture 120 to allow for coupling of IUD 110 and suture 120.

In the illustrated embodiment, needle 130 and suture 120 can again be directed through coupling mechanism 125 after exiting second channel 152 such that suture 120 creates a loop 128 in uterine cavity 160. Suture 120 can be positioned so that a first end 121 of suture 120 (e.g. the end of suture 120 directed into uterine cavity wall 140) and a second end 122 of suture 120 extend from coupling mechanism 125.

Figure 6:
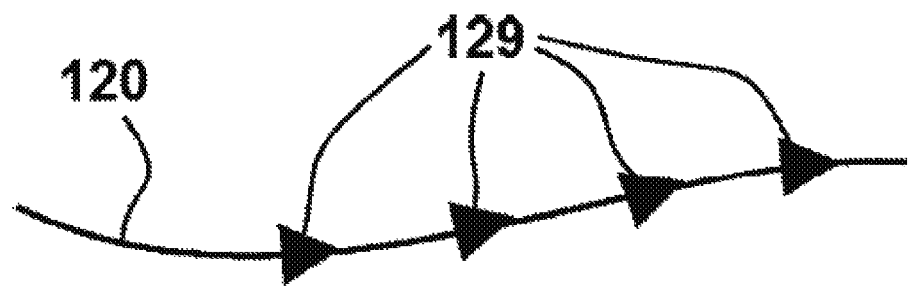
FIG. 6 illustrates a detailed view of a suture of the embodiment of FIGS. 1-5.

In exemplary embodiments suture 120 may be configured as a barbed suture, with barbs that allow suture 120 to be advanced into uterine cavity wall 140 in only one direction. For example, suture 120 may include barbs 129 (shown in FIG. 6) that allow suture 120 to be inserted into tissue (e.g. uterine cavity wall 140) in one direction, but do not allow suture 120 to be retracted from tissue in the opposite direction. Accordingly, with suture 120 shown in position in FIG. 5, suture 120 can be advanced and removed from uterine cavity wall 140 by pulling on first end 121, allowing IUD 110 to also be removed from uterine cavity 160. Specifically, suture 120 and IUD 110 can be removed by pulling on first end 121 of suture 120 until second 122 has been advanced through IUD 110 uterine cavity wall 140. However, a force exerted on second end 122 will not allow suture 120 to be removed from uterine cavity wall 140. Such a configuration can allow for secure placement of IUD 110 in uterine cavity 160 and decrease the likelihood of unintentional removal of IUD 110 from uterine cavity 160.

Figure 7:
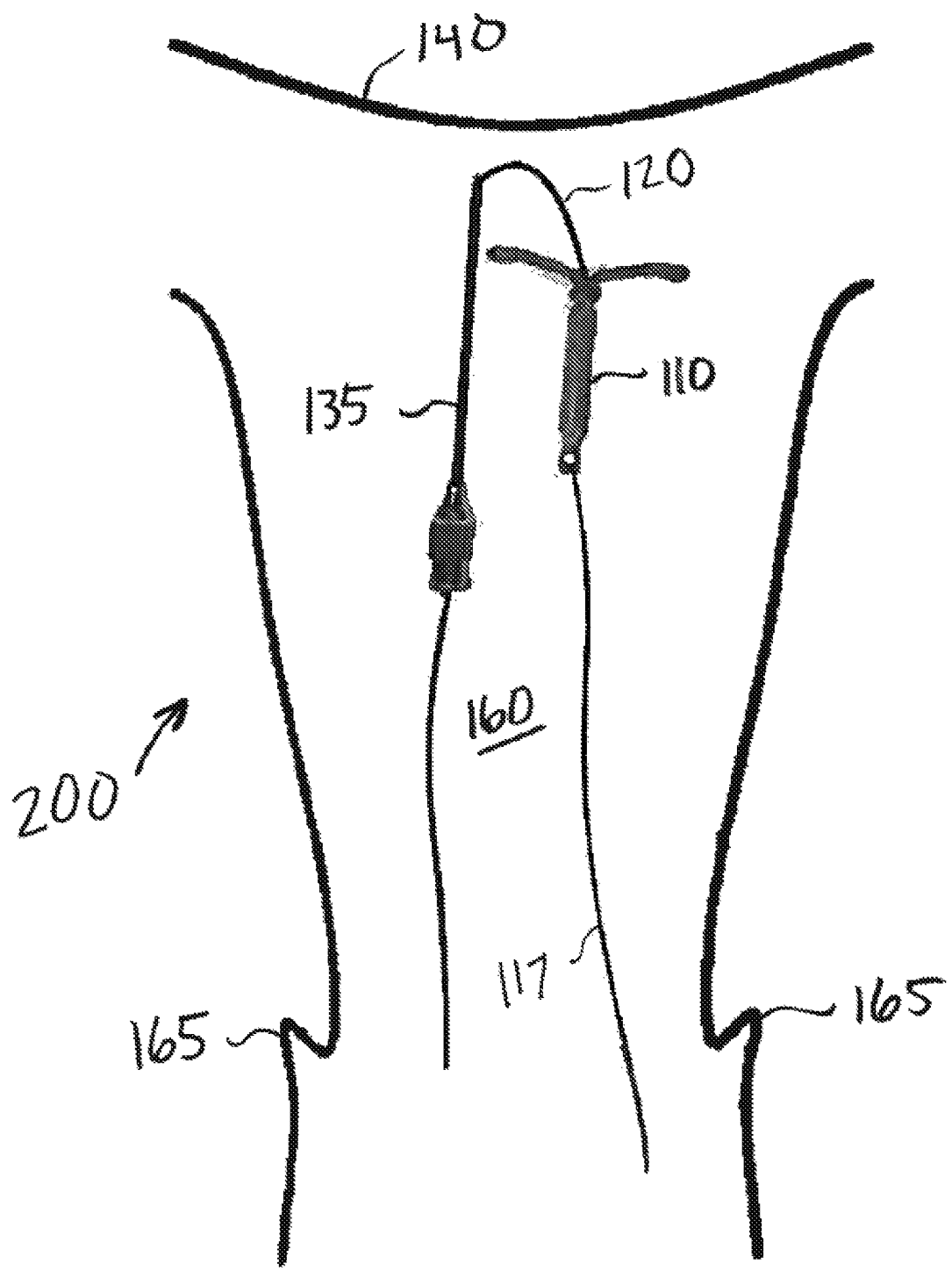
FIGS. 7-8 illustrate a second exemplary embodiment of a system and method of securing an IUD as disclosed herein.
Figure 8:
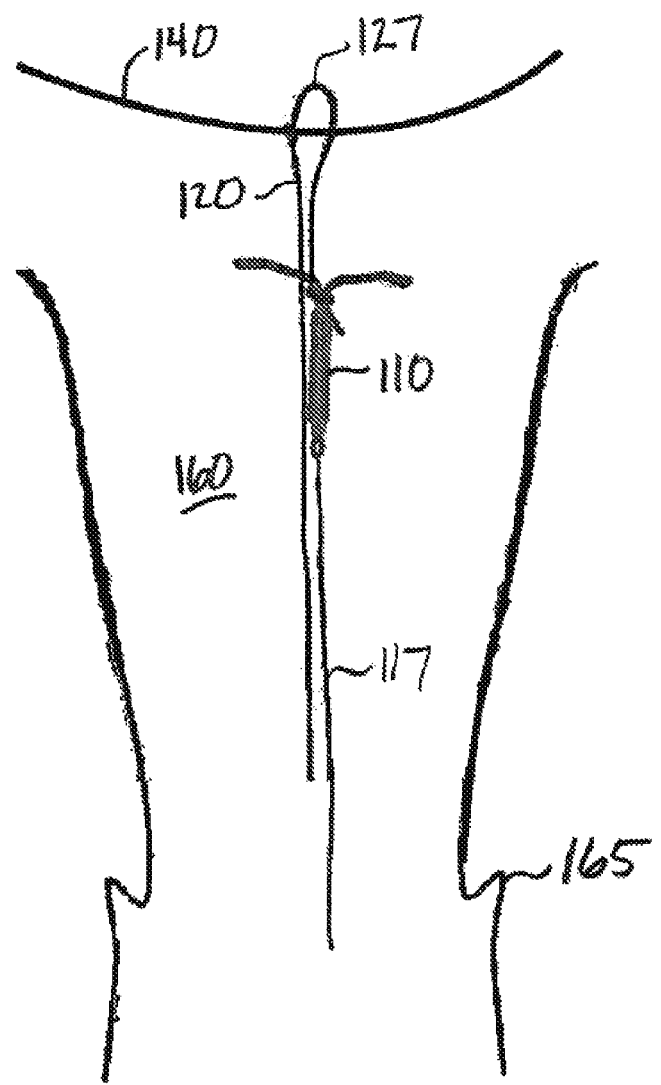

In other embodiments, IUD 110 may be inserted into uterine cavil 160 and secured to uterine cavity wall 140 without the use of suction device 150. Referring to FIGS. 7 and 8, a needle 135 can be used to directly insert suture 120 into uterine cavity wall 140 (including, for example, the fundus). In this embodiment, IUD 110 is configured as a T-shaped IUD rather than the frameless configuration shown in FIGS. 1-5. It is understood that different configurations of IUDs (including those eluding novel drugs) are compatible with different insertion techniques as disclosed herein.

In particular embodiments, needle 135 is a commercially available sterile needle and suture 120 is a barbed suture. Specific examples of such barbed sutures include the V-Loc™ Absorbable Wound Closure Device product line available from Covidien, Mansfield, Ma. and the Quill™ SRS bidirectional barbed suture product line available from Angiotech Pharmaceuticals, Inc., Vancouver, BC, Canada. In specific embodiments, suture 120 can be a biodegradable suture that is designed to release IUD 110 after a specified period of time (e.g. a period of weeks or months). In certain embodiments, suture 120 is biocompatible but not configured to degrade and release IUD 110 in a specified time period. In such embodiments, removal of IUD 110 can be accomplished by pulling on a release device a string or cord) coupled to IUD 110 as described more fully below.

In the embodiment shown in FIGS. 7 and 8, a clinician can insert a loop of suture 120 into the uterine fundus using needle 135. The clinician can then retract and dispose of needle 135. In exemplary embodiments, the shaft length of needle 135 will ensure the loop of suture 120 is inserted appropriately and reliably into the myometrium (muscle layer) of the uterine cavity wall 140 without perforating the wall. In the embodiment shown, a cord 117 is coupled to IUD 110 and extends from uterine cavity 160 and cervix 165.

When desired, IUD 110 can be removed from uterine cavity by pulling on cord 117 in a direction away from uterine cavity wall 140. This can allow suture 120 to be released from uterine cavity wall 140 and allow for the removal of suture 120, IUD 110 and cord 117 from the uterine cavity. In certain embodiments, cord 117 may extend approximately 1 centimeter past cervix 165 to allow for access when removal of IUD 110 is desired.

Figure 9:
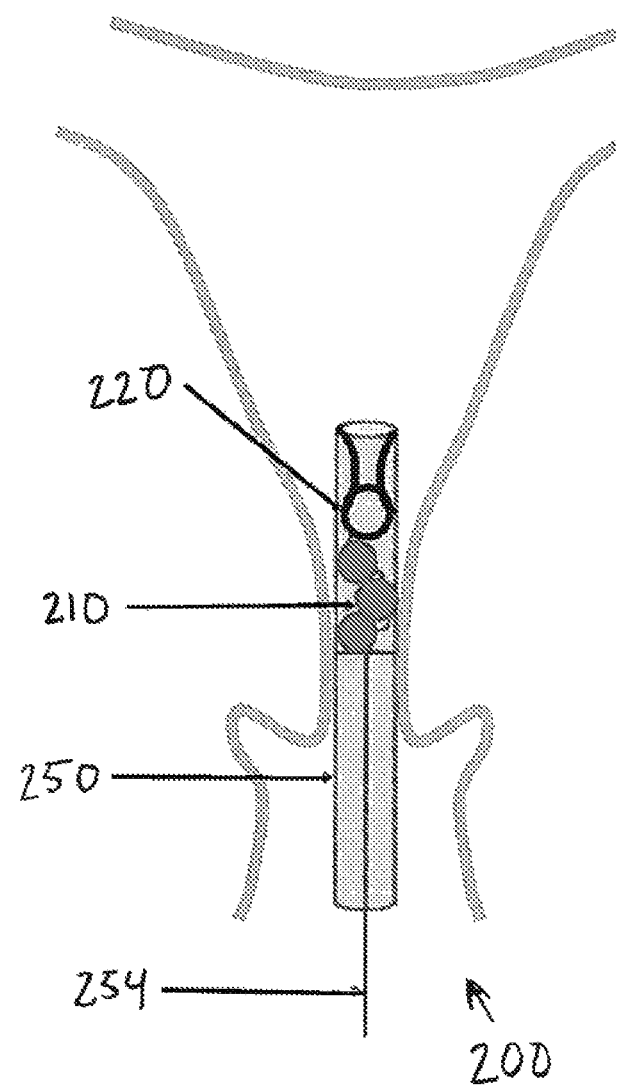
FIGS. 9-11 illustrate a third exemplary embodiment of a system and method of securing an IUD as disclosed herein.
Figure 10:
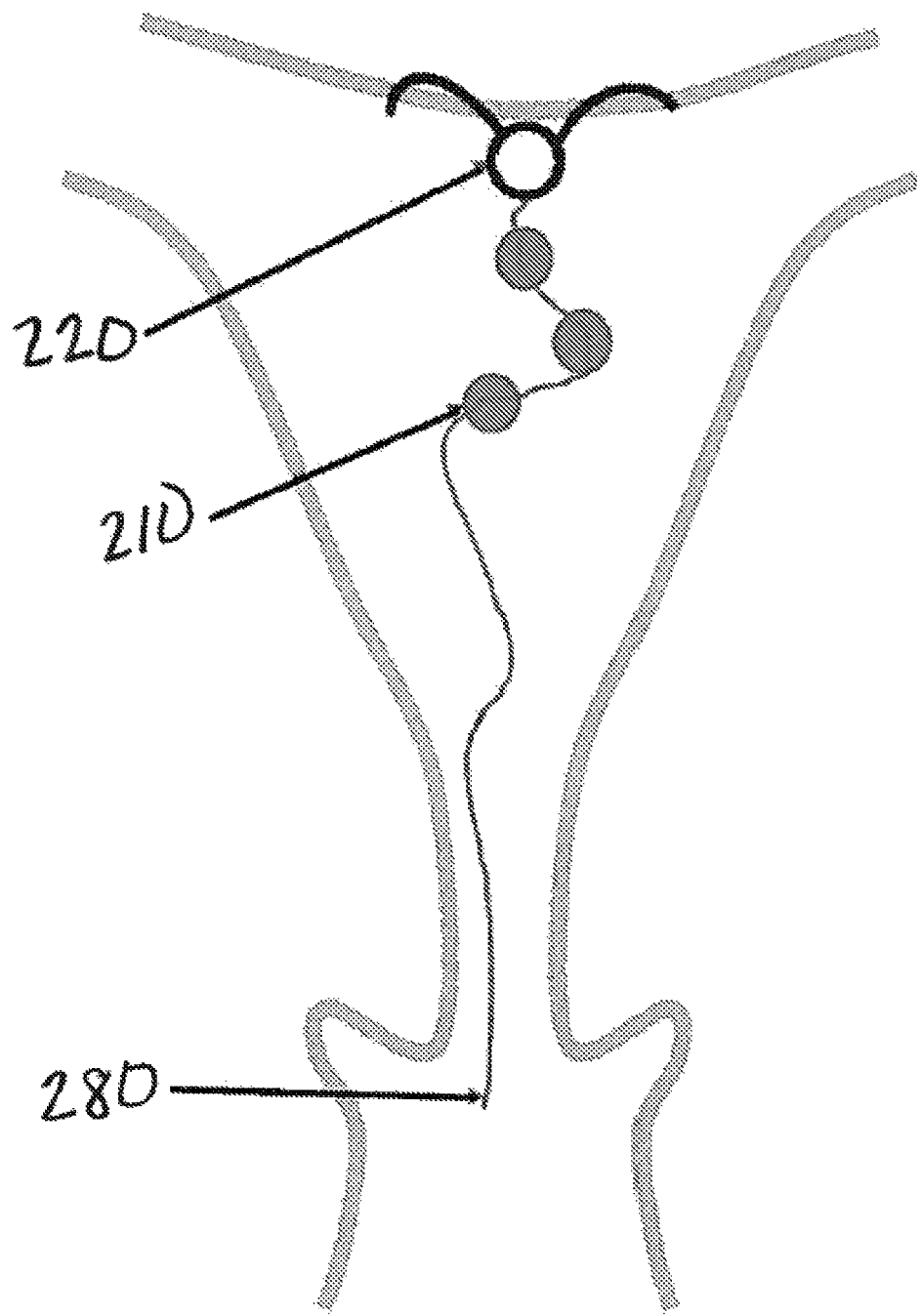
Figure 11:
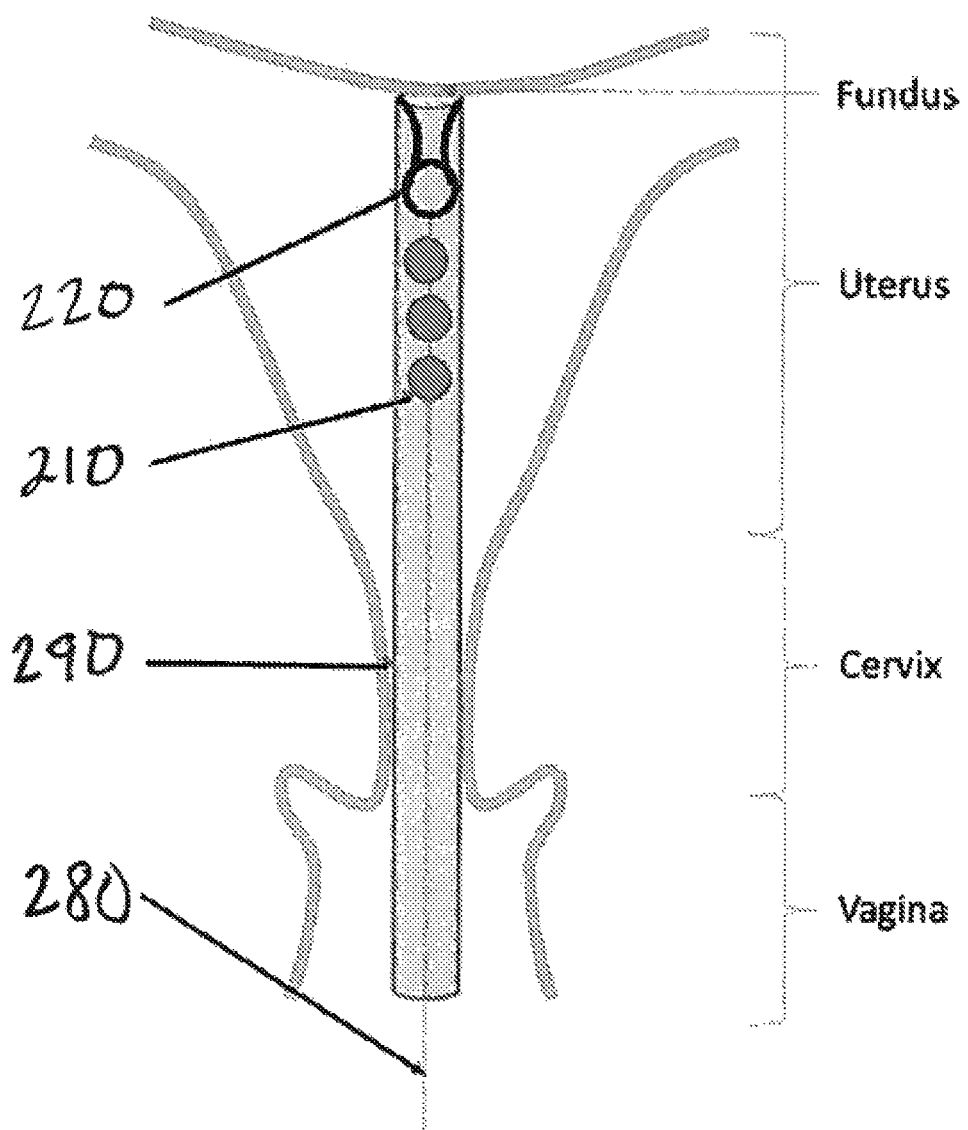

Referring now to FIGS. 9-11, a system 200 includes an IUD 210 with an anchor 220 instead of a barbed suture as disclosed in previous embodiments. FIG. 9 illustrates IUD 210 in an insertion step, FIG. 10 in a deployed state, and FIG. 11 in a removal step. In certain embodiments, IUD 210 is small and frameless (e.g. without a metal or plastic frame like currently available T-framed IUDs), and comprises a string with several copper or LNG eluding spherical beads. This can allow IUD 210 to fully adapt to uterus environmental changes including contractile forces from multiple and varied directions. The frameless design can be beneficial for adapting to the geometrical changes the uterus undergoes after giving birth (e.g. during PP involution). Additionally, the frameless IUD can reduce concern for device perforation after deployment.

As shown in FIG. 9, IUD 210 is anchored to the fundal wall. This helps to ensure that IUD 210 remains in place to prevent IUD migration, perforation, and expulsion, despite the contractile forces or geometrical alterations that occur in the uterus during involution or regular menstrual periods. Although IUD 210 is anchored to the uterine fundus (endometrium/myometrium), its unique design does allow for a "release mechanism" for removal that is comparable to current IUDs (e.g. via a string or cord 280 protruding from the cervix).

In certain embodiments, anchor 220 comprises a hook-anchor concept similar to other medical anchoring devices (including for example, the Medtronic® Micra Transcatheter Pacing System). In certain embodiments, IUD 210 can be coupled directly to the anchor 220. In particular embodiments, the applicator remains comparable to current IUD technology in terms of geometrical constraints presented by the cervix and uterus, but also provides mechanical feedback to inform the clinician when they have reached the fundus. This can be especially important during PP, where navigation to the fundus is more difficult. Research has indicated the importance of IUD deployment at the fundus to not only reduce expulsion rates, but also improve contraceptive efficiency [17].

The applicator employs a long thin insertion tube 250 that houses IUD 210 and a concentric plunger 254 to initiate device deployment. The plunger mechanism also contains a spring-like resistive feedback to the clinician to let them know when they have reached the fundal wall. At this point, the clinician actuates the plunger for the anchor system, and the spring-like anchor 220 hooks into the uterine fundus. It is important to note that the applicator can also be used in post-Cesarean-section births by inserting the applicator through the uterine incision rather than the cervix.

IUD 210 can be removed in a similar way to which it was inserted. An inexpensive removal tube 290 can be placed around string 280 that protrudes from the cervix. Removal tube 290 can then be fed through the cervix, guided by string 280 to the base of anchor 220. The distal end of tube 290 can be configured to fit around anchor 220, stabling the fundal tissue to prevent stretching and tearing during removal of anchor 220.

The clinician can then pull on string 280 extending through tube 290, which retracts the uniquely designed anchor hooks. With the hooks locked in the retracted position within tube 290, along with beads of IUD 210 and thread 280, retraction tube 290 is safely removed from the uterus, cervix, and vagina, leaving no components in place.

Figure 12:
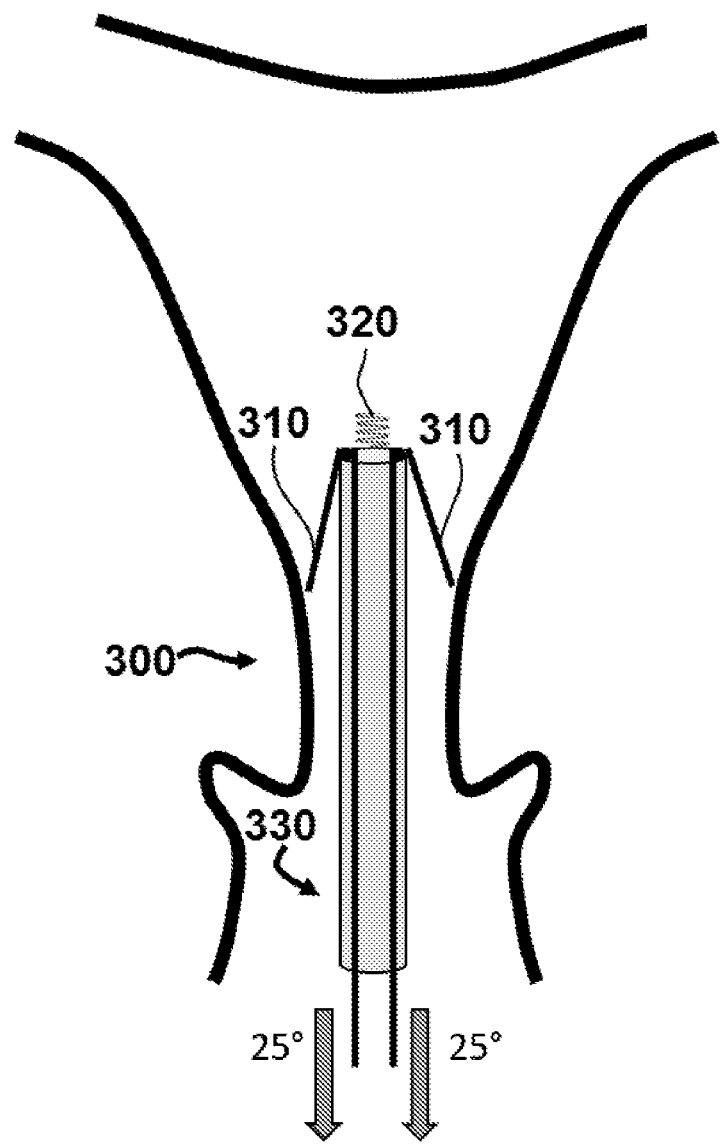
FIGS. 12-26 illustrate additional embodiments of systems and methods of securing an IUD as disclosed herein.
Figure 13:
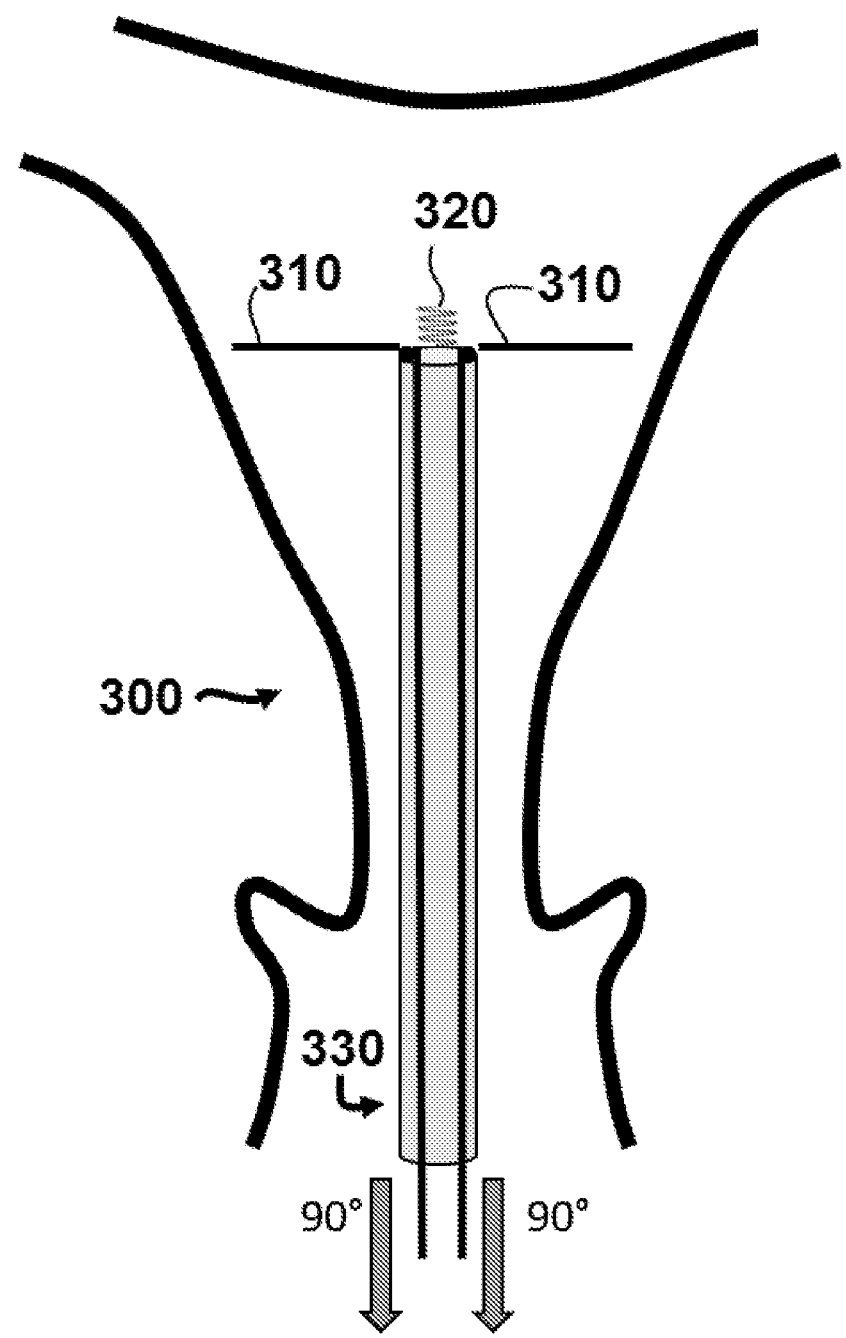
Figure 14:
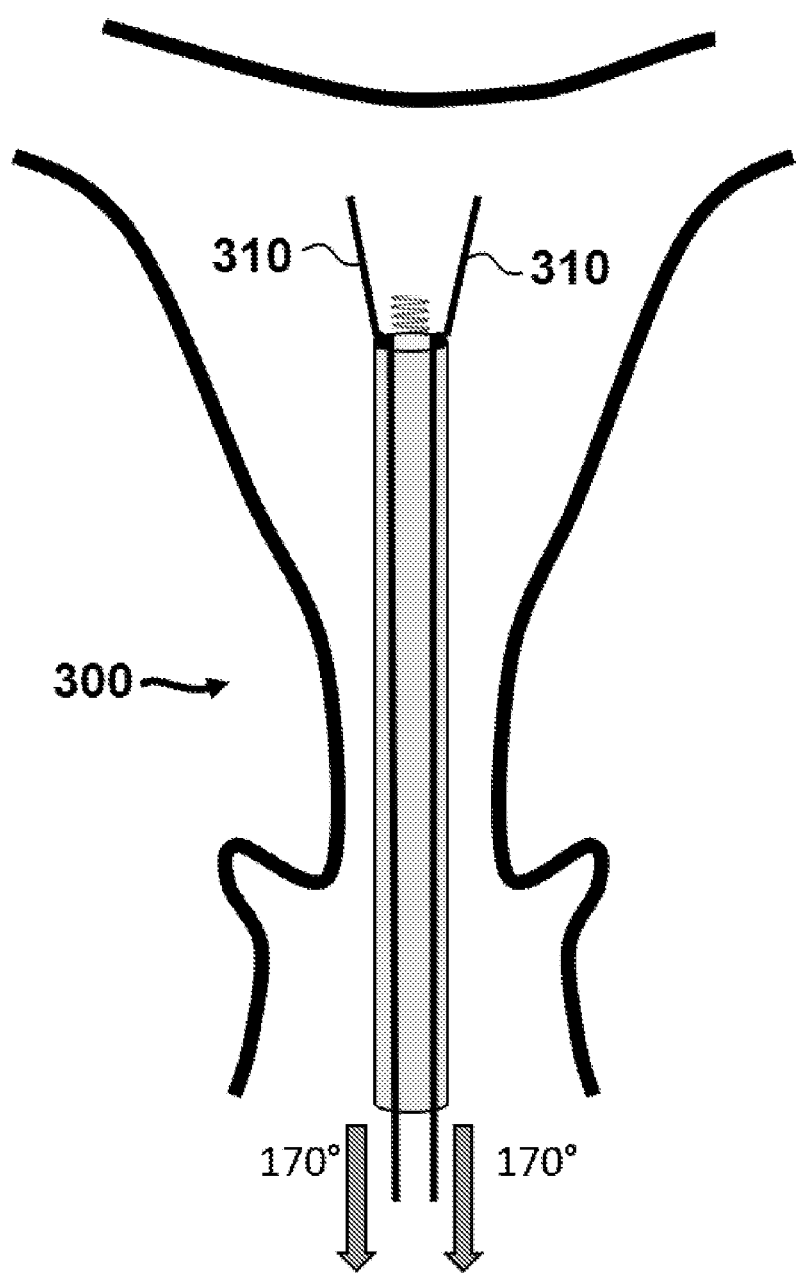
Figure 15:
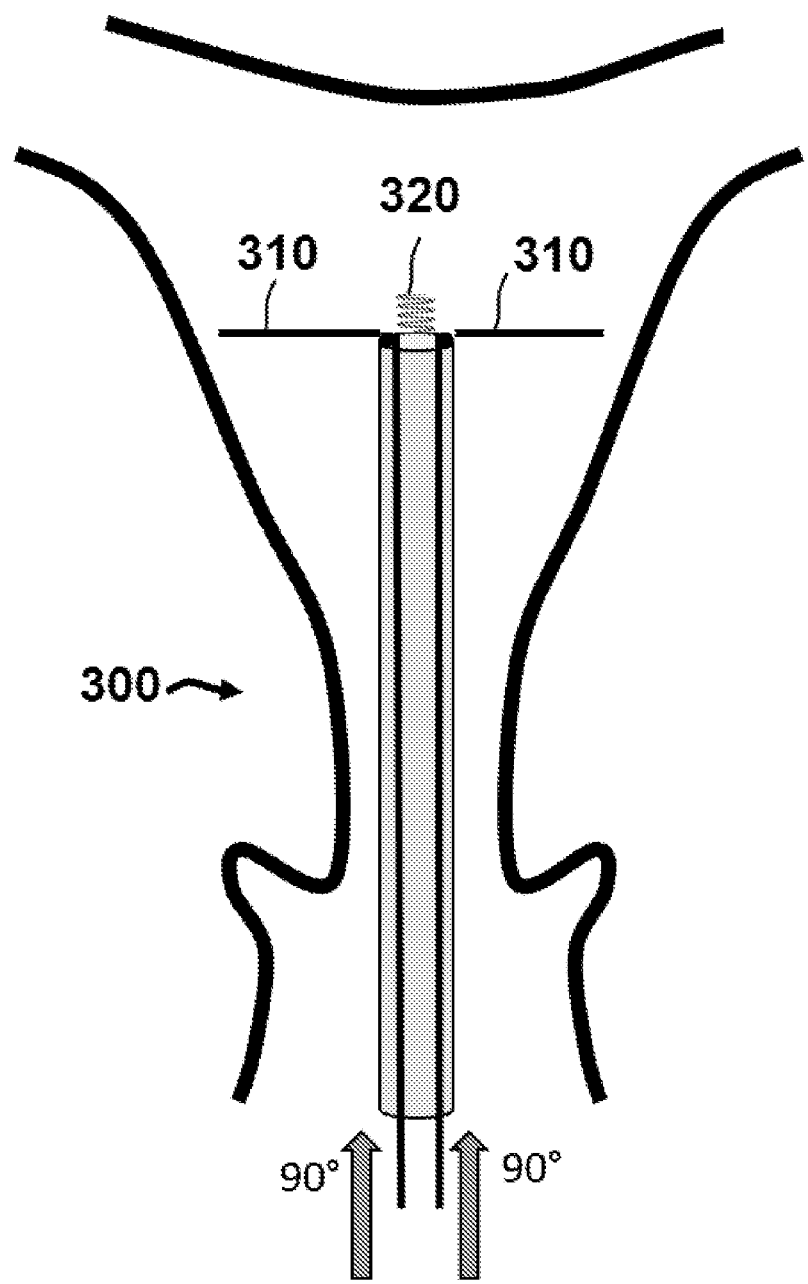
Figure 16:
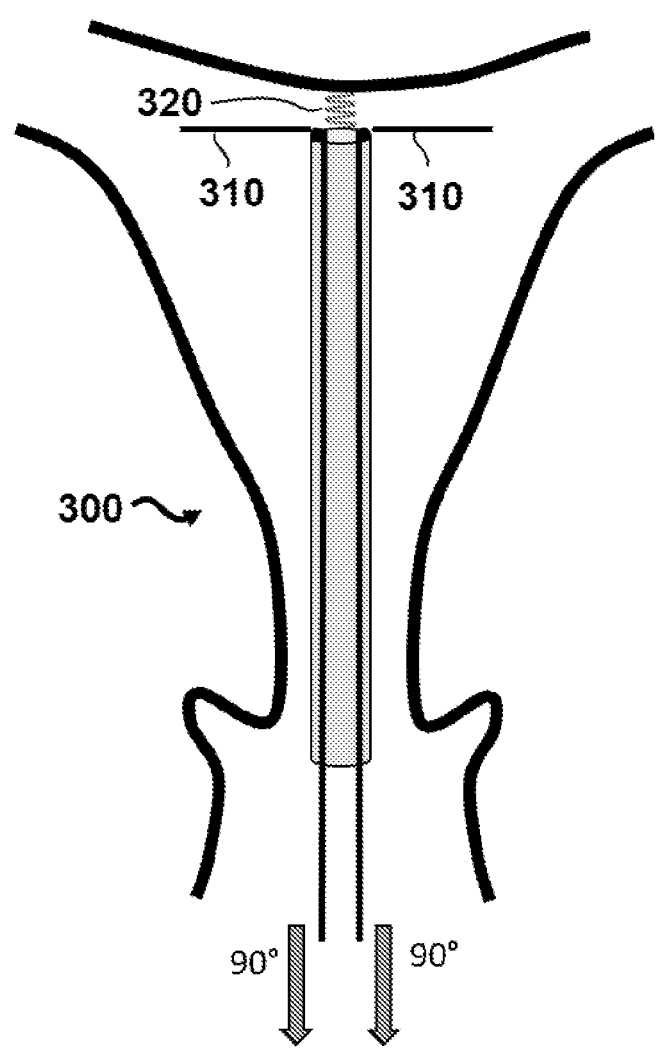
Figure 17:
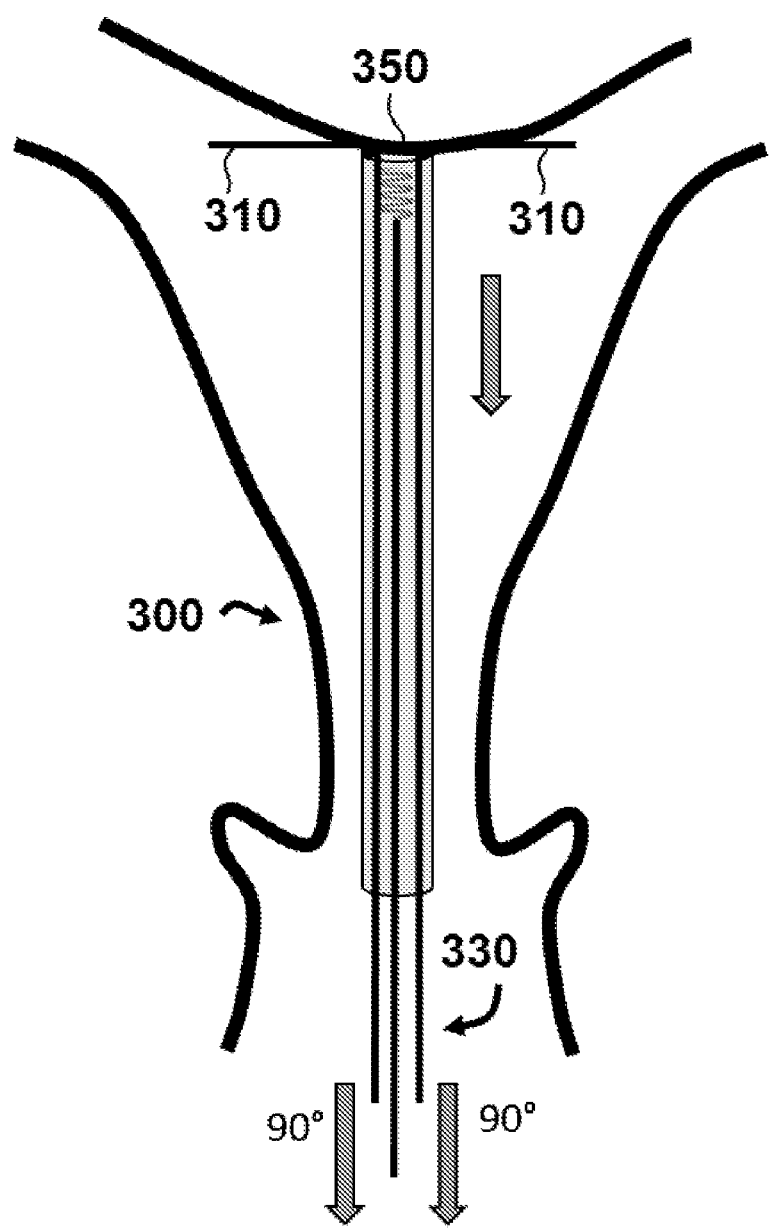
Figure 18:
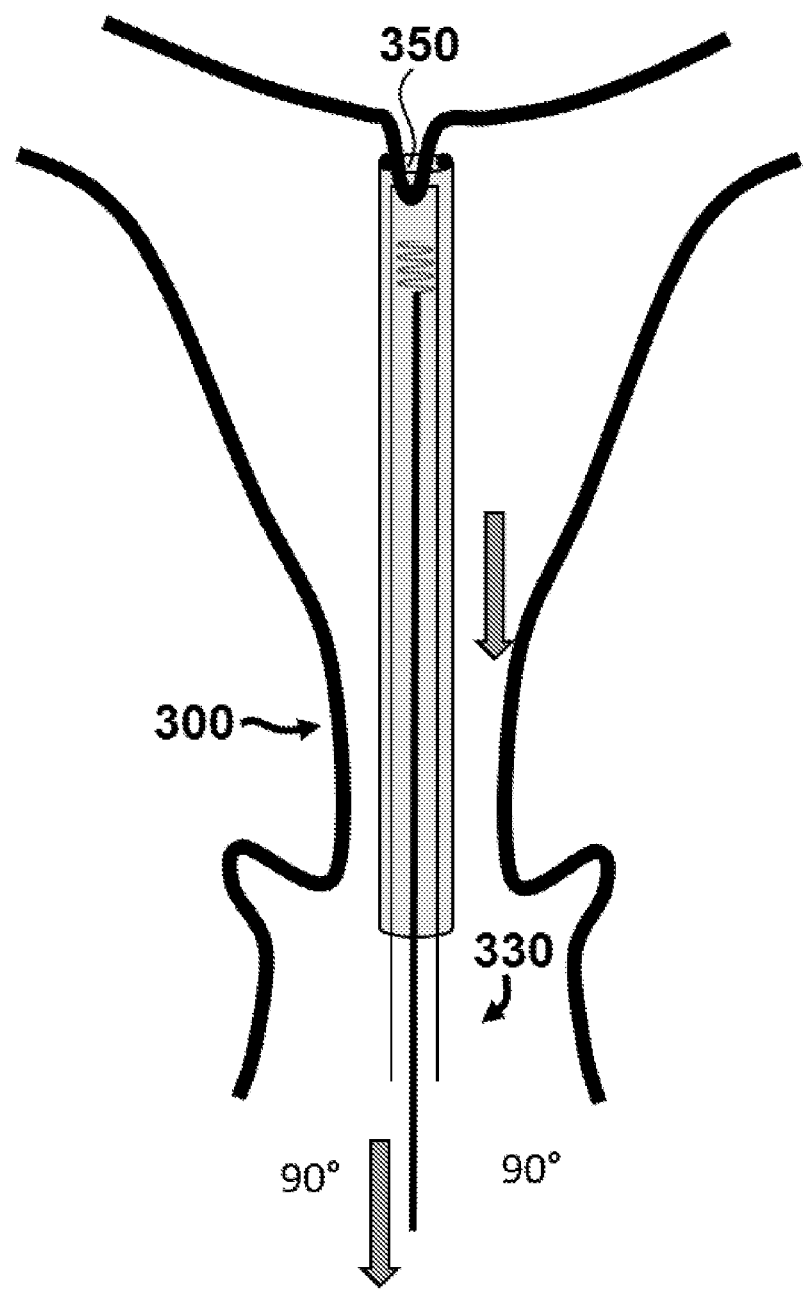
Figure 19:
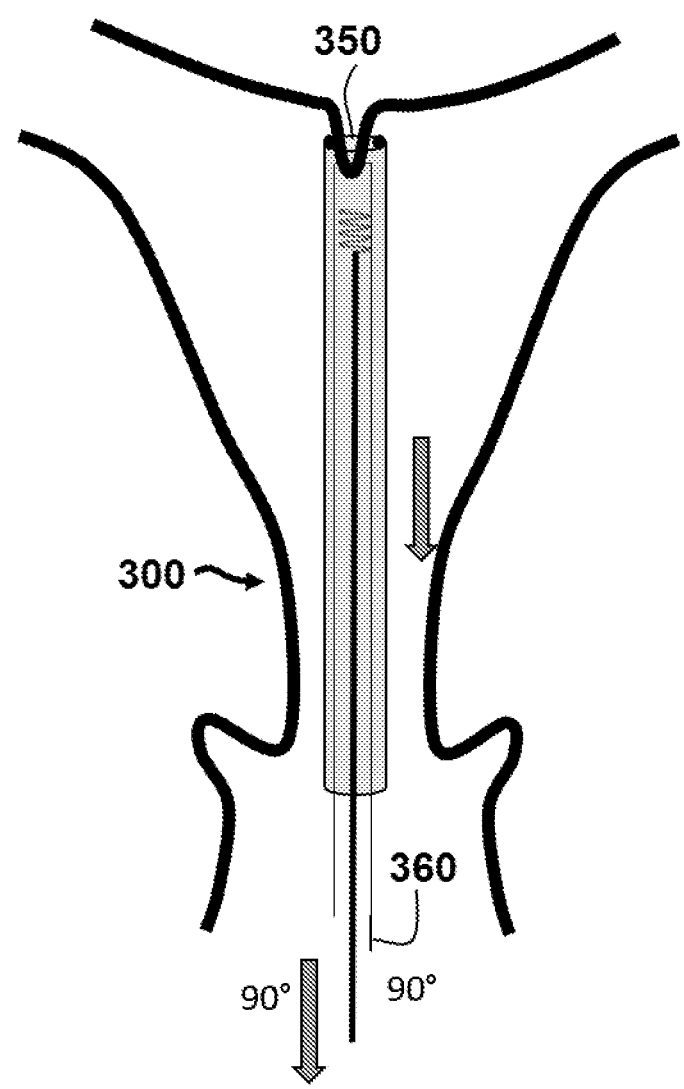
Figure 20:
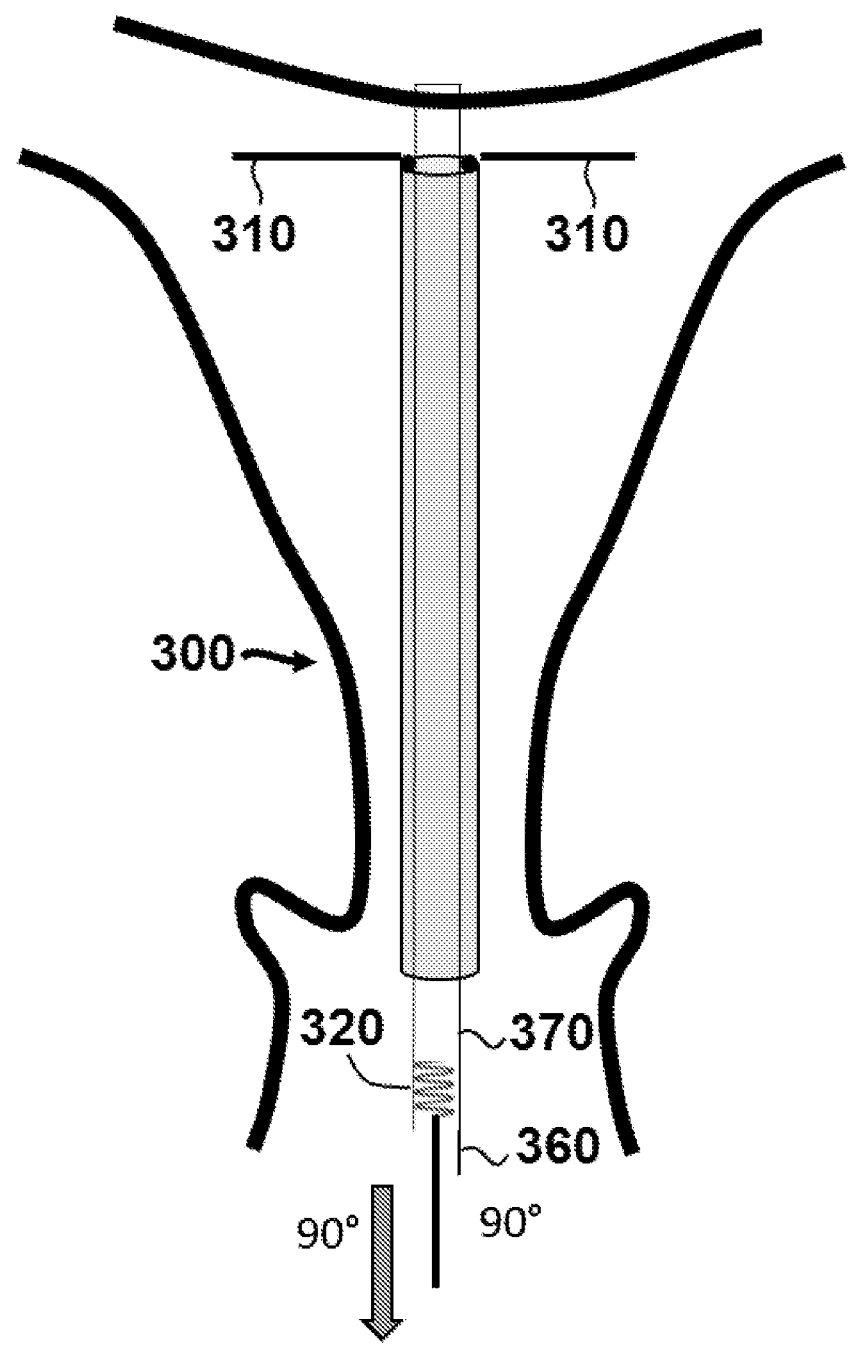
Figure 21:
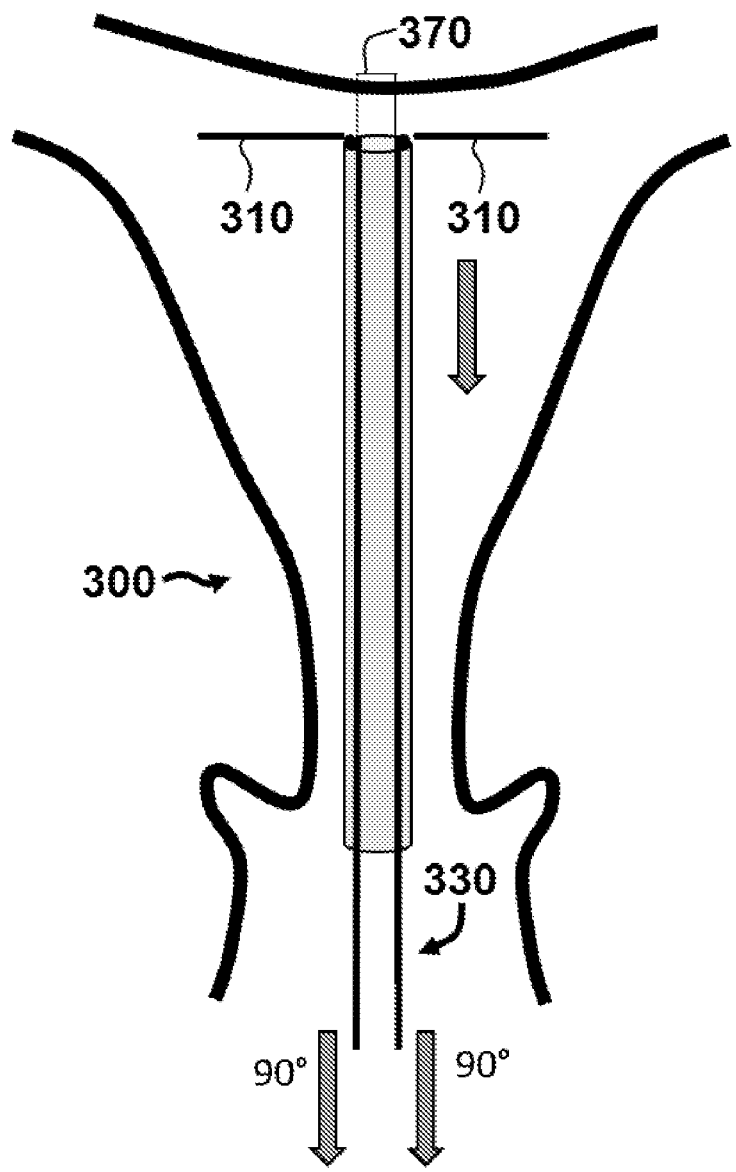
Figure 22:
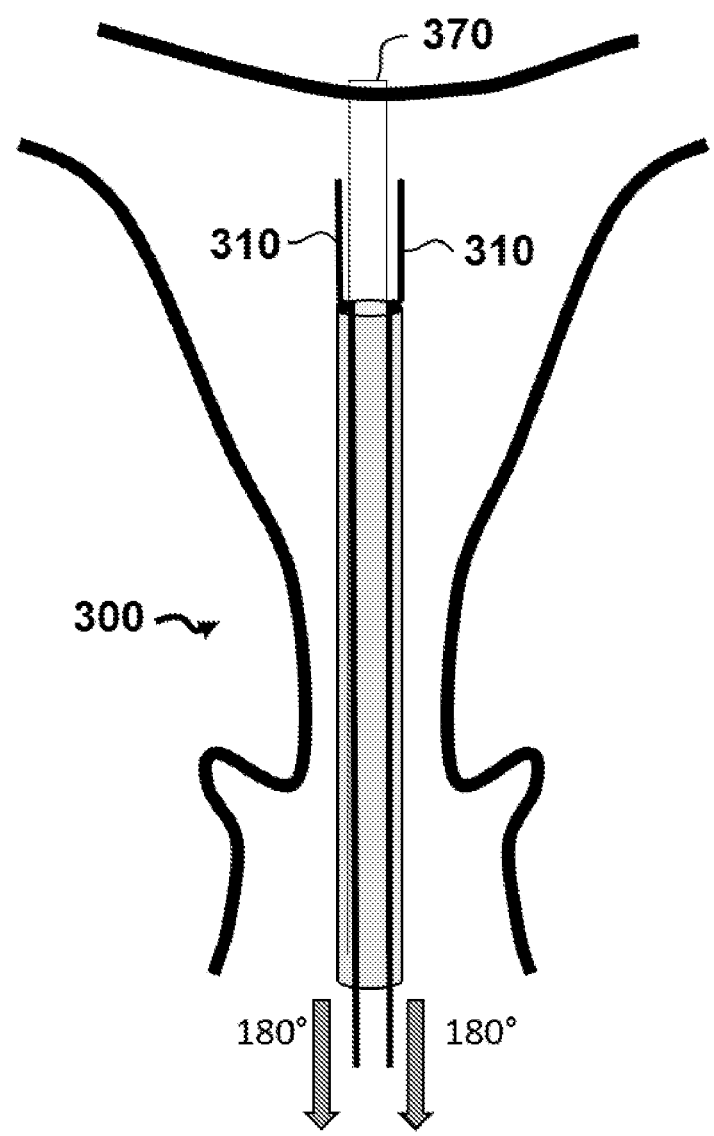
Figure 23:
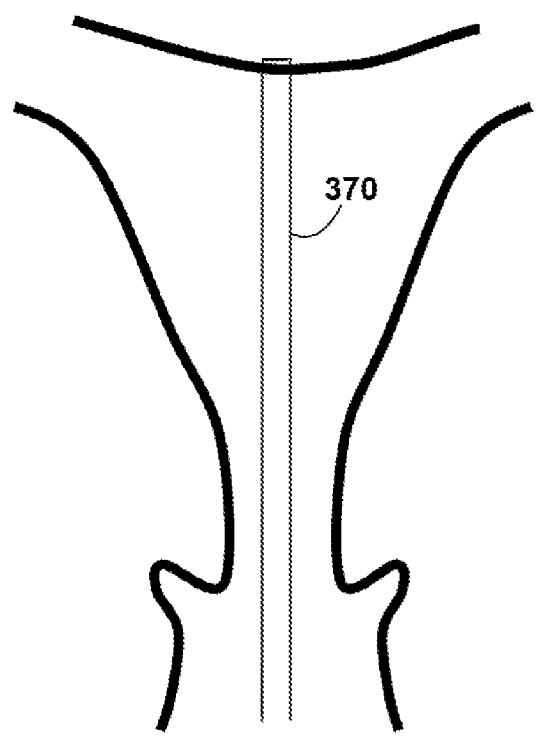

FIG. 12 illustrates an embodiment of a system 300 with a spring 320 and arms 310 shown in a position that contact al the uterine wall rather than the fundus. As discussed further below, arms 310 can be extended separately via control mechanisms 330 (e.g. rods that can be pushed or pulled to pivot arms 310) to provide unique feedback (arm angle, distance, length, pitch resistance, etc.). FIG. 13 shows arms 310 not contacting the uterine wall at 90 degrees as system 300 is advanced into the uterine cavity. There is no contact with the fundus in this position, so spring 320 does not provide any feedback. In FIG. 14, arms 310 have been repositioned to extend approximately 170 degrees from a primary axis of system 300, but still do not contact the fundus. This can confirm to the user that system 300 has not advanced too far into the uterine cavity. In FIG. 15, arms 310 have been returned to a position at approximately 90 degrees. In FIG. 16, system 300 has been advanced until spring 320 provides resistive feedback to a user when contacting the fundus. In FIG. 17, spring 320 has been retracted, causing a vacuum to draw a target region of the fundus into an inner conduit 350 of system 300. In FIGS. 18 and 19, fundal tissue is held in inner conduit 350 as a needle 360 is guided through a loop or slot in system 300 that directs needle through the nodal tissue. Note that arms 310 are not shown in FIGS. 18 and 19 for purposes of clarity. In FIG. 20, spring 320 is removed from system 300 and the vacuum can be released. In FIGS. 21 and 22, arms 310 can be positioned to allow system 300 can be removed from the uterine cavity. FIG. 23 illustrates a string 370 that can function as an IUD contraceptive component (or from which IUD contraceptive components can be anchored). Certain embodiments may include a mechanical constraint to ensure string 370 does not move more than desired with respect to the fundus.

Figure 24:
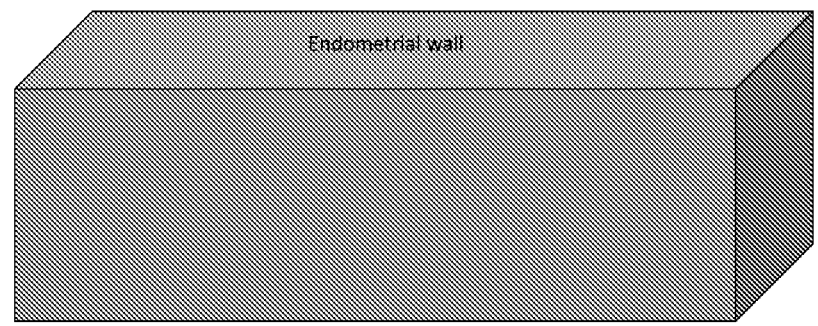
Figure 24:
Figure 25:
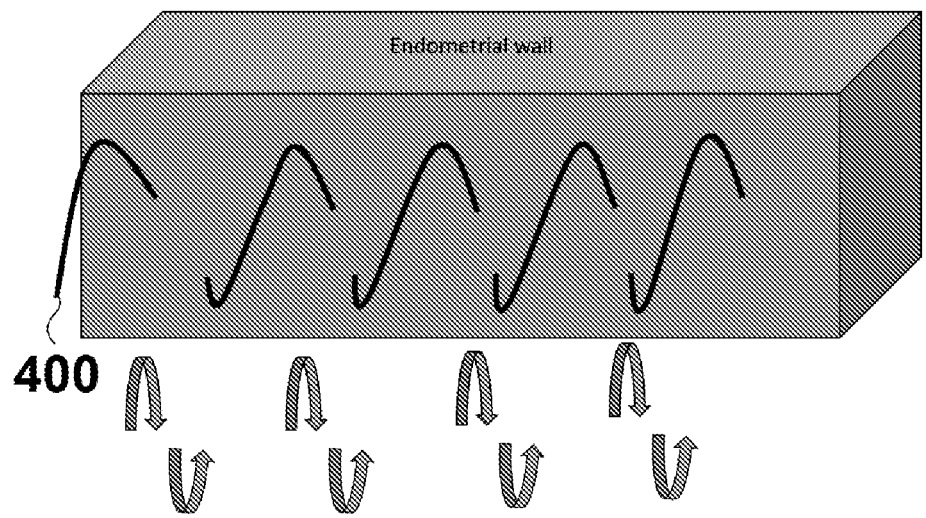

FIGS. 24 and 25 illustrate an embodiment with an anchor mechanism 400 configured as a coil spring that can be anchored into an endometrial wall. In FIG. 24, anchor mechanism 400 is shown adjacent to the endometrial wall, and in FIG. 25, anchor mechanism 400 is shown anchored to endometrial wall by rotating anchor mechanism 400 proximal to the wall sot that it penetrates and advances into the wall). The stretchable and compressible nature of the coil spring configuration allows anchor mechanism 400 to stretch and compress if the wall tissue is similarly manipulated by stretching or compressing.

For purposes of clarity, not all elements in every figure are labeled with reference numbers. In certain figures, for example, elements that are labeled in other figures may not be labeled due to different positioning of components in the figures.

EXAMPLES

The following examples are included to demonstrate exemplary embodiments of the disclosure. It should be appreciated by those of skill in the art that the techniques disclosed in the examples which follow represent techniques discovered by the inventor to function in the practice of the disclosure, and thus may be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Figure 26:
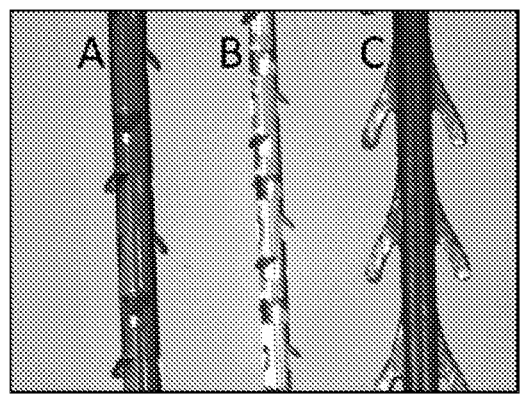

Tested sutures included two Covidien V-Loc barbed sutures (180 day absorption profiles, at gauge levels of 3-0 and 0-0) and an Ethicon Stratafix Symmetrical suture (PDS Plus, at a gauge level of 1-0). FIG. 26 shows a magnified view of barbed sutures used during experimentation: (A) Covidien V-Loc 0-0, (B) Covidien V-Loc 3-0, (C) Ethicon.

An experimental setup was used to collect preliminary data. Sutures were inserted using a 14 gauge hypodermic needle with a 60° bevel angle, and placed in the top clamp, which in turn was attached to a 2 kN Dynacell load cell that was linked with the lab's Instron Electropuls e1000 universal mechanical testing machine. The experiment was completed in two separate segments: insertion and removal For the insertion portion of the experiment, the suture was threaded into the needle and the suture-needle combination was secured in the top clamp. A custom tissue fixture mount including a tissue clamp stage to contain the tissue was then secured in the bottom clamp. Readily available raw beef tongue (room temperature) was used to simulate uterine tissue, as clinical interviews suggested this might be an easily obtained tissue that is somewhat comparable in consistency to uterine tissue due a somewhat muscular/tough composition. The tissue clamp stage was then tightened to a total height of 20 mm for round 1 of experiments, and 10 mm for round 2, around the tissue specimen in an effort to prevent undesirable tissue deflection, and improve reliability and consistency of suture insertion depths. The tissue clamp stage includes a small insertion hole that the needle and suture can pass through, as well as a small cavity within the wooden base of the fixture that allows for the needle-suture combination to pass all the way through the tissue specimen without impacting or contacting the mounting fixture. The suture-needle combination was lowered to a zero-point at near-contact with tissue that presented no significant load. This zero position was then set and locked using the Instron program capabilities in order to maintain the near-contact distance between tissue and needle for each individual trial. Once the load cell was balanced/tared to negate the weight of the suture-needle combination, the needle-suture combination was driven 23.5 mm through the tissue at a constant rate of 10 mm/s, extending slightly beyond the tissue to an open cavity underneath the tissue specimen (so as not to damage the needle or load cell, or introduce experimental errors). By extending beyond the tissue levels and into the cavity, the team is able to confirm that the maximum amount of tissue engaging with sutures were limited to the designated insertion depths of 20 and 10 mm, therefore improving consistency and reliability of the experimental procedure and results. During insertion, the load cell measured the force over time as the first major output.

After insertion, without moving the suture-needle combination, the clamp was loosened, and then raised a small distance to allow for manual removal of the needle from the tissue, while the barbed suture remained unmoved and embedded in the tissue. The engaged end of the suture (end that is not housed in the needle, and would typically be secured to IUD) was then secured in the top clamp. The suture was then removed using the Instron machine. The top clamp in conjunction with the load cell pulled the suture out of the tissue, while measuring the change in force over time.

The beef sample was adjusted before each insertion round to ensure that a new, unaffected tissue segment was used for suture insertion and removal. The suture was rinsed and cleaned of all tissue residue, and gently dried using a paper towel. Finally, the suture was further dried/cleaned using compressed air to ensure that no contaminants were left on the suture.

Results and Discussion

A summary table of key data points can be seen in Table 1 below. It will be noted that insertion forces (i.e. compressing the load cell) show as positive values while removal forces (i.e. tensioning the load cell) show as negative values.

TABLE 1

| INSERTION | 20 mm Insertion Depth Maximum Insertion Force (grams-force) | 10 mm Insertion Depth Maximum Insertion Force (grams-force) |
| --- | --- | --- |
| V-Loc Gauge 0-0 | 712.810 ± 71.104 | 621.140 ± 26.225 |
| V-Loc Gauge 3-0 | 473.390 ± 42.919 | 394.550 ± 67.724 |
| Stratafix Symmetrical Gauge 1-0 | 667.140 ± 27.533 | 548.68 ± 15.725 |
| REMOVAL | Maximum Retention Force (grams-force) | Maximum Retention Force (grams-force) |
| V-Loc Gauge 0-0 | −184.100 ± 44.564 | −118.500 ± 15.540 |
| V-Loc Gauge 3-0 | −78.220 ± 10.886 | −98.040 ± 33.437 |
| Stratafix Symmetrical Gauge 1-0 | −299.500 ± 22.405 | −209.180 ± 67.286 |

The data in Table 1 shows required insertion and retention forces varied between suture types and insertion depths. It appears clear that lower insertion forces are required for sutures with smaller diameter gauges (i.e. less volume/bulk), seeing as the suture with the most nominal gauge (i.e. V-Loc, gauge level 3-0) required the smallest amount of force for insertion into tissue, while the 1-0 gauge and 0-0 gauge sutures were noticeably higher in required insertion force, respectively. However, it will also be noted that the Stratafix Symmetrical 1-0 required an insertion force closer to that of the V-Loc 0-0 gauge, likely due to its more pronounced, bulky profile. Conversely, higher gauges levels also appeared to correlate to higher retention forces, with a notable caveat. When comparing performance between the two V-Loc sutures, the smaller diameter gauge (i.e. 3-0) was nearly half as strong in ability to withstand removal forces for the 20 mm insertion depth. However, the Stratafix Symmetrical 1-0 gauge outperformed the V-Loc 0-0 gauge with an average maximum retention force of nearly 300 grams-force compared to roughly 184 grams-force, respectively, despite having a lower gauge profile. Compared to the weight of an average IUD trainer (approximately 0.5 grams), even the weakest average retention force measured has a safety factor valued at over 100. Similar trends were similarly seen in the 10 mm insertion depth, though there appear to be more variation in the data.

Figure 27:
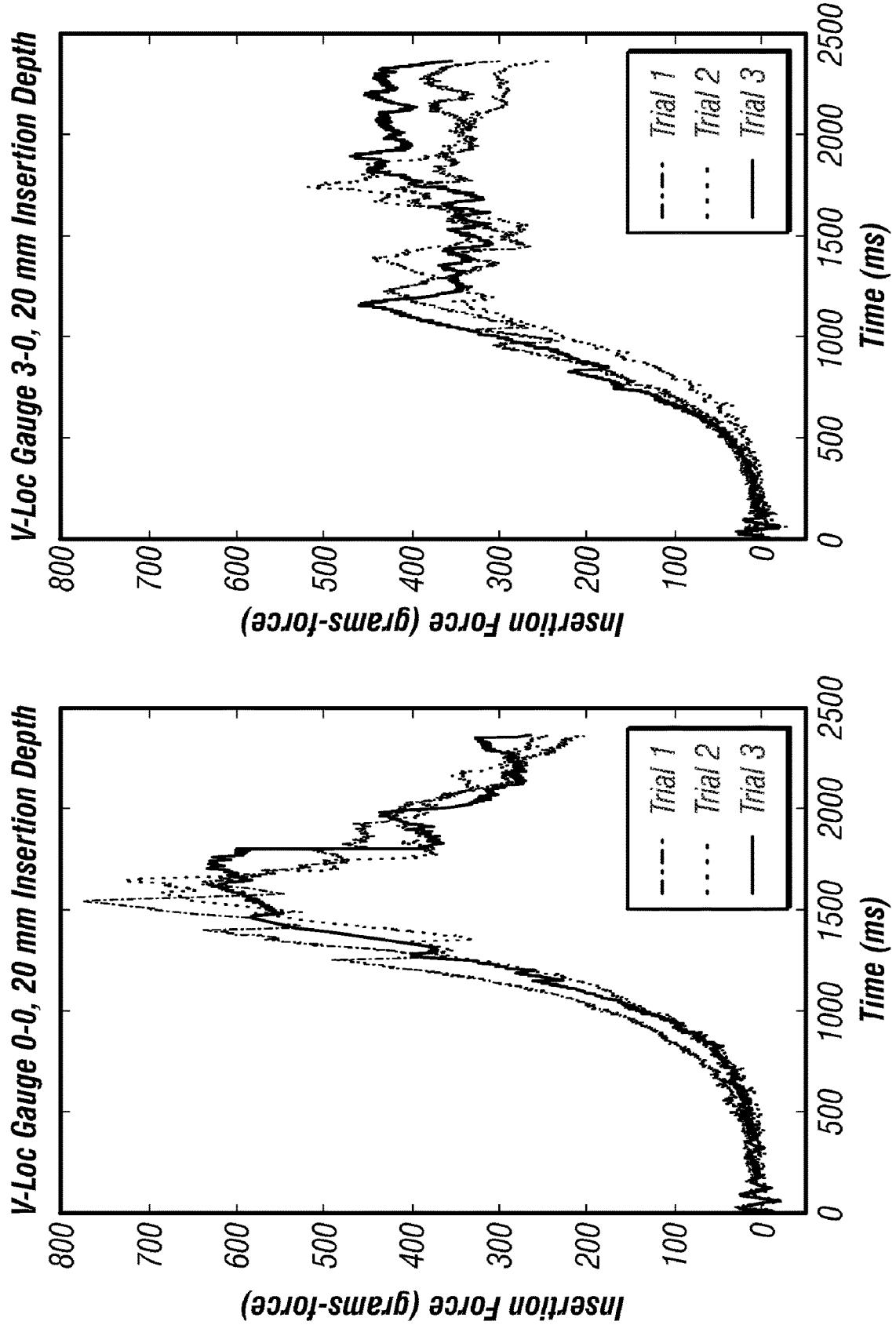
FIGS. 27-28 illustrate graphs of data obtained during testing of components of exemplary embodiments.
Figure 27:
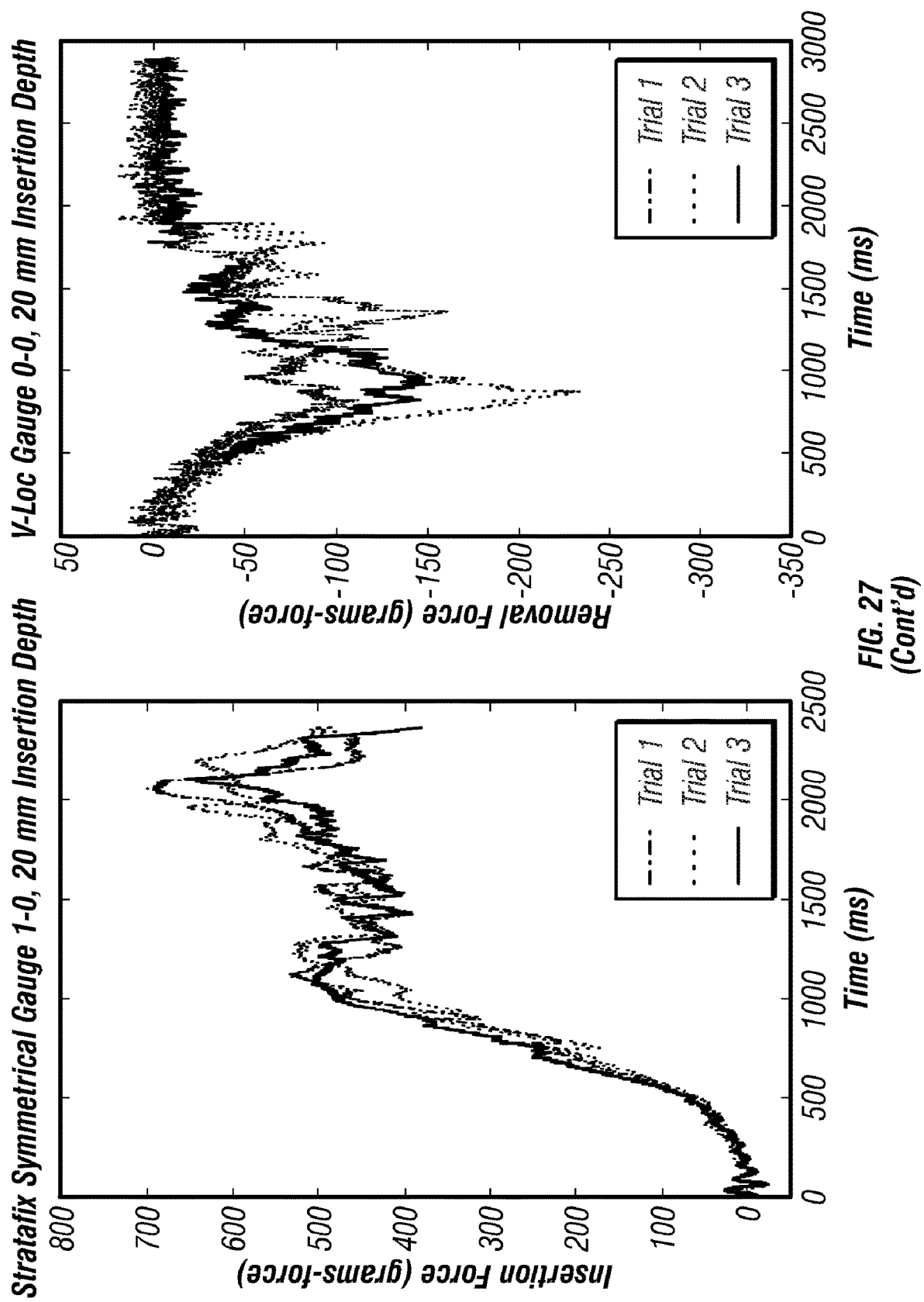
Figure 27:
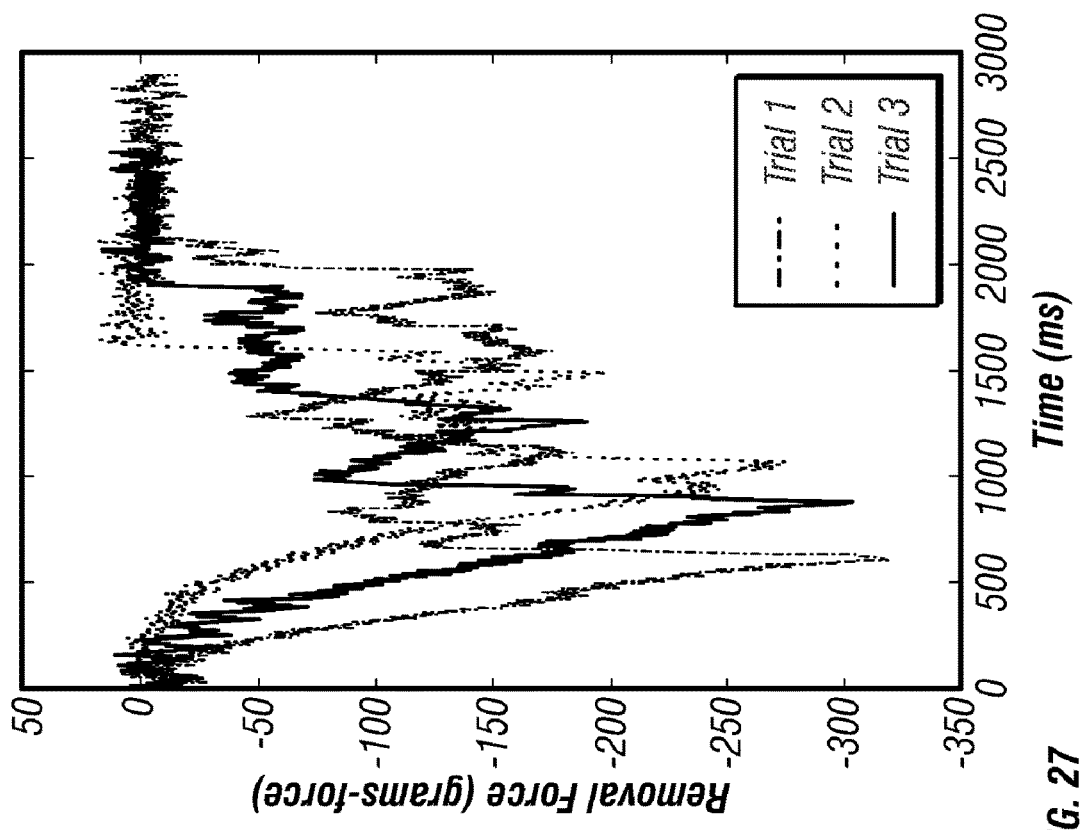
Figure 27:
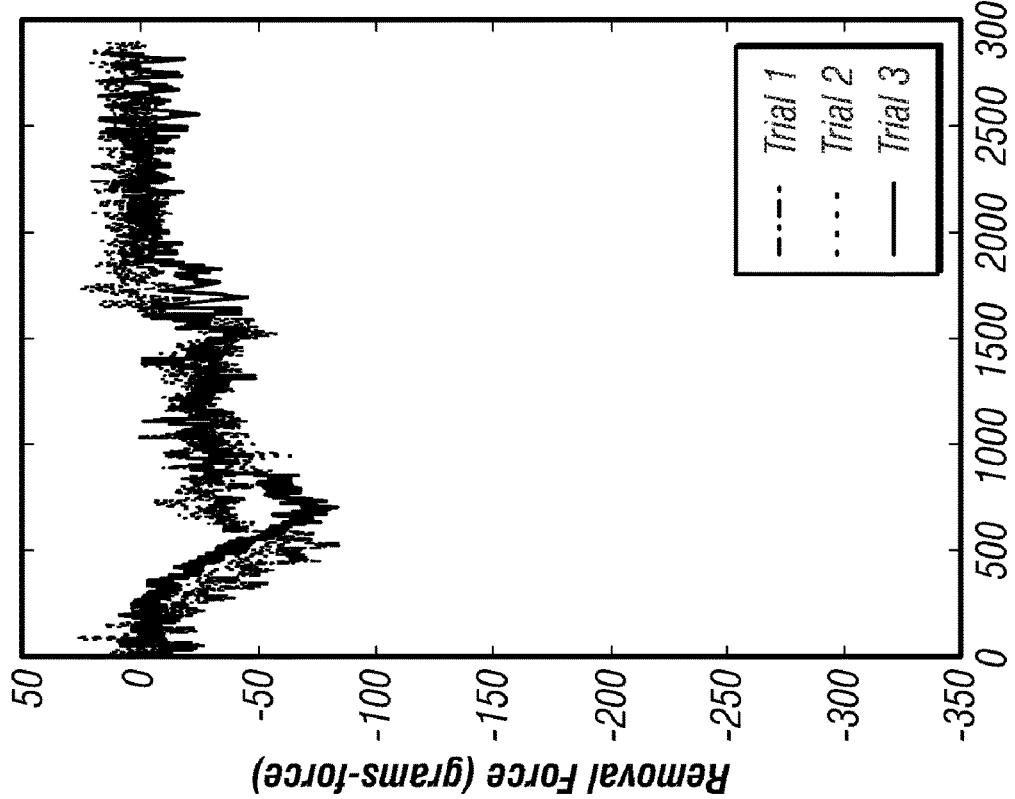
Figure 28:
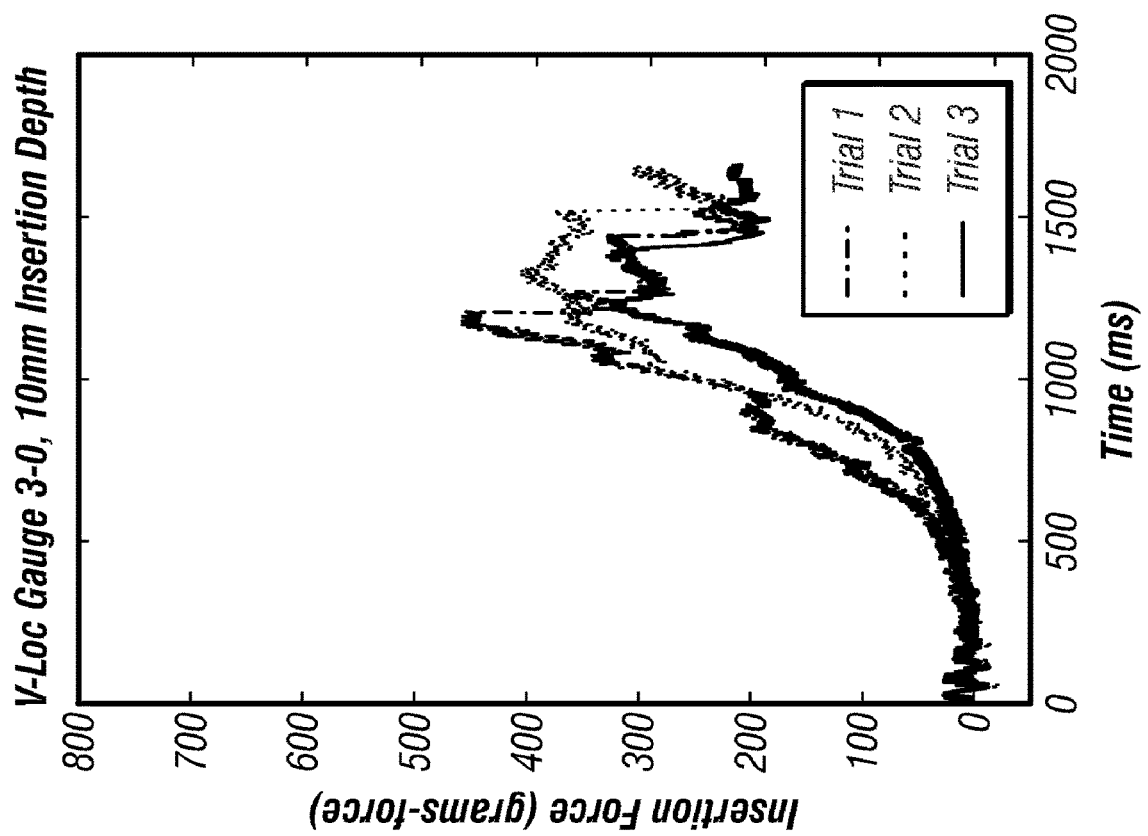
Figure 28:
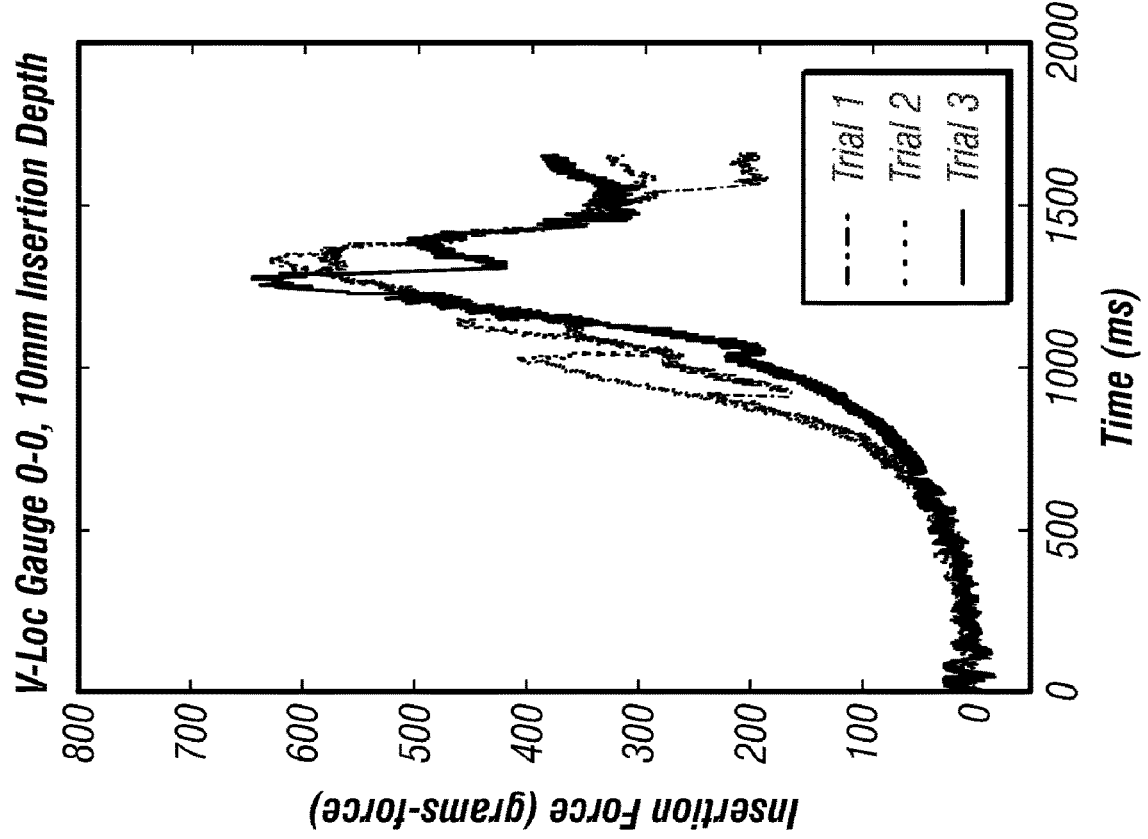
Figure 28:
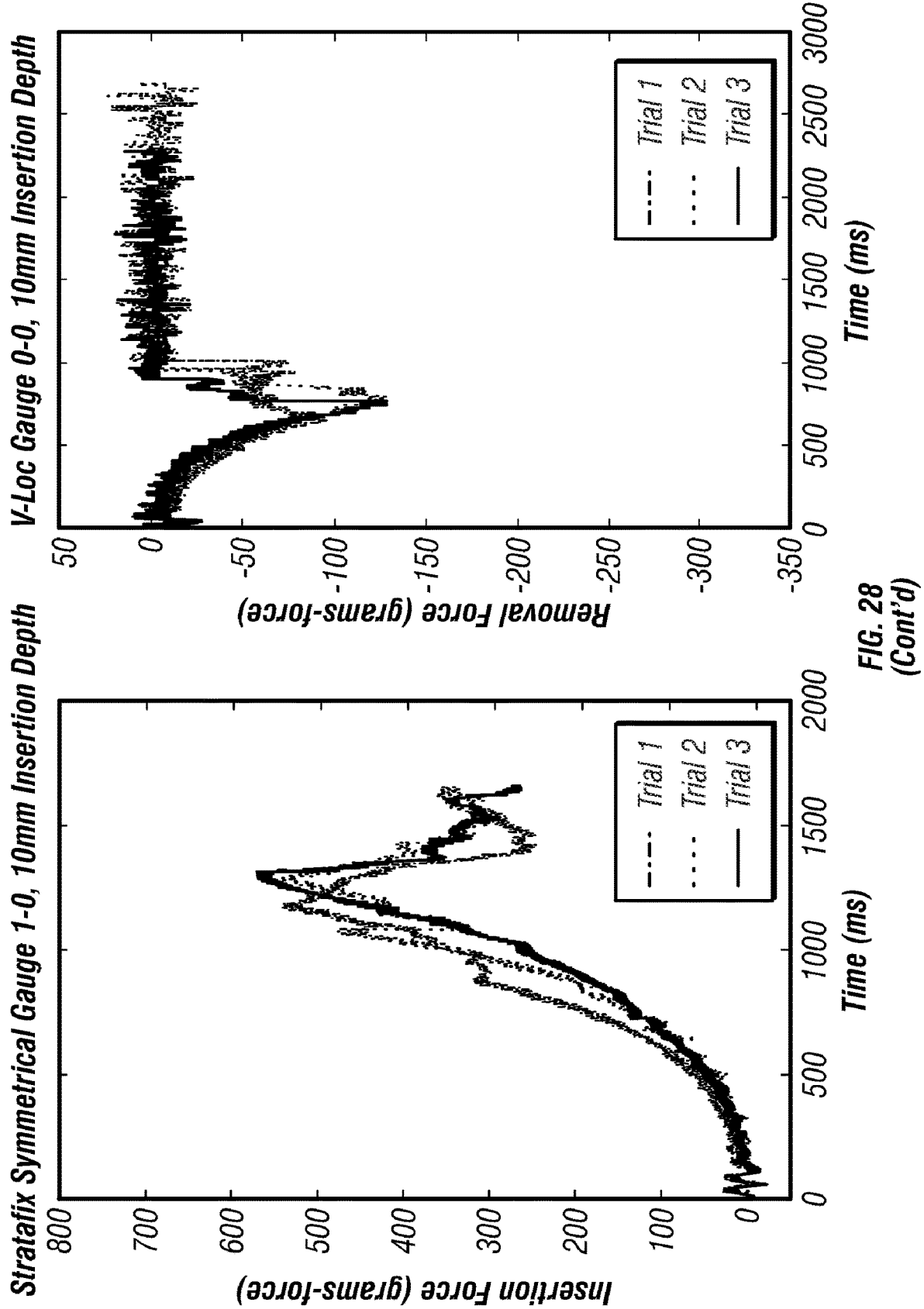
Figure 28:
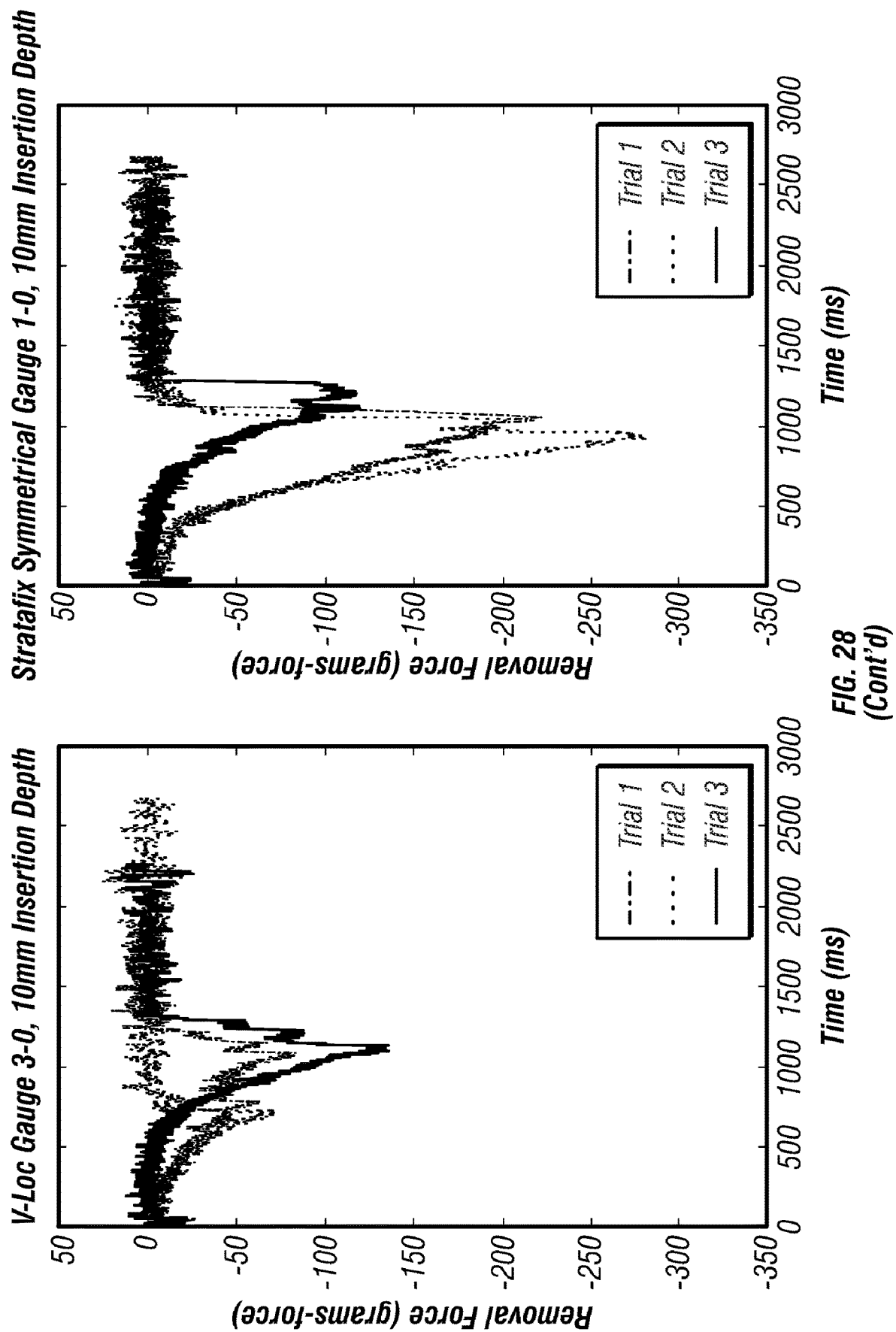

Additional graphs of data relating to trials for insertion and removal experiments can be found in FIGS. 27-28. FIG. 27 illustrates data of suture insertion and removal trials for 20 mm insertion depth and FIG. 28 shows data of suture insertion and removal trials for 10 mm insertion depth.

In FIGS. 27-28, trials (n=3) of both insertion and removal experiments for each type of suture tested are shown. Graphs are maintained at the same scale for all insertion experiments and likewise for all removal experiments to allow for easier visual translation for the reader. Time is measured in milliseconds, and force is measured in grams-force.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
U.S. Pat. No. 4,005,707
U.S. Pat. No. 4,684,369
U.S. Pat. No. 4,708,134
U.S. Pat. No. 4,721,105
U.S. Pat. No. 5,433,218
U.S. Pat. No. 5,303,717
U.S. Pat. No. 5,433,218
U.S. Pat. No. 6,588,429
U.S. Pat. No. 6,742,520
U.S. Pat. No. 7,080,647
WO 1991000714
US 20120318276
WO 2014111533
US 20150359663
CA 2064026 C
EP 2515806
CN 102525723
WO 2013061341
WO 2010112095
WO 2014041120
CN 201283028 Y
EP 2770959
CA 2784602
WO 2011080164
CN 201642510 U
1. Medtronic, *Micra Transcatheter Pacing System*. Medtronic, 2016.
2. Sperzel, J., et al., *State of the art of leadless pacing*. European Society of Cadriology, 2015.
3. Chi, I., L. Wilkens, and S. Rogers, *Expulsions in immediate postpartum insertions of Lippes Loop D and Copper T IUDs and their counterpart Delta devices—An epidemiological analysis*. Contraception, 1985. 32(2): p. 119-134.
4. Kapp, N. and K. Curtis, *Intrauterine device insertion during the postpartum period: a systematic review*. Contraception, 2009. 80: p. 327-336.
5. *Highlights of the Percy Skuy History of Contraception Gallery: Intrauterine device (IUD)*. Case Western Reserve University, Percy Skuy Collection, 2000.
6. Service, U.D.o.H.a.H., *Contraception: Effectiveness of Family Planning Methods*. US Department of Health and Human Service, Center for Disease Control and Prevention, 2011.
7. WHO, *Report of a WHO Technical Consultation on Birth Spacing*. WHO, 2005.
8. Mosher, W., C. Moreau, and H. Lantos, *Trends and determinants of IUD use in the USA, 2002-2012*. Human Reproduction, 2016. 0(0).
9. Lopez, L., et al., *Immediate postpartum insertion of intrauterine device forcontraception (Review)*. Cochrane Database of Systematic Reviews, 2015(6).
10. Celen, S., et al., *Clinical outcomes of early postplacental insertion of intrauterine contraceptive devices*. Contraception, 2006. 69: p. 279-282.
11. Eroglu, K., et al., *Comparison of efficacy and complications of IUD insertion in immediate postplacental/early postpartum period with interval period: 1 year follow-up*. Contraception, 2006. 74: p. 376-381.
12. Hayes, J., et al., *A pilot clinical trial of ultrasound-guided postplacental insertion of a levonorgestrel intrauterine device*. Contraception, 2007. 76: p. 292-296.
13. Morrison, C., et al., *Clinical outcomes of two early postpartum IUD insertion programs in Africa*. Contraception, 1996. 53: p. 17-21.
14. Roepke, C. and E. Schaff, *Long Tail Strings: Impact of the Dalkon Shield 40 Years Later*. Open Journal of Obstetrics and Gynecology, 2014. 4(16): p. 996-1005.
15. Dennis, J., A. Webb, and M. Kishen, *Expulsions following 1000 GyneFix insertions*. The Journal of Family Planning and Reproductive Health Care, 2001. 27(3): p. 135-138.
16. Wildemeersch, D., et al., *Intrauterine Contraception in Adolescent Women The Gynefix Intrauterine Implant*. Annals of the New York Academy of Sciences, 1997. 816(440-450).
17. Wildemeersch, D., et al., *Efficacy of a mini version of the frameless GyneFix intrauterine system (IUS) with effective copper surface area of 200 mm2*. Contraception, 2002. 66(4): p. 237-241.
18. *Mirena: IUD Insertion*. drugwatch, 2016.
19. Laerdal, Reinvigorating the Postpartum IUD Using a Low-Cost Siomulation Model. Jhpiego, an affiliate of Johns Hopkins University, 2011.
20. Laerdal, *Mama-U: Postpartum Uterus Trainer*. Laerdal: Healping save lives, 2016.
21. Honglian, *GD/F5N IUD Training Simulator*. General Doctor, 2016.
22. Liecthy, E., I. Bergin, and J. Bell, *Animal models of contraception: utility and limitations*. Open Access Journal of Contraception, 2015. 6: p. 27-35.
23. Baram, I., A. Weinstein, and J. Trussell, *The IUB, a newly invented IUD: a brief report*. Contraception, 2014. 89(2): p. 139-141.
24. Wiebe, E. and J. Trussell, *Discontinuation rates and acceptability during 1 year of using the intrauterine ball (the SCu380A)* Contraception, 2016. 93(4): p. 364-366.
25. Zhou, L., M. Harrison-Woolrych, and D. Coulter, *Use of the New Zealand Intensive Medicines Monitoring Programme to study the levonorgestrel-releasing intrauterine device (Mirena)*. Pharmacoepidemiology and Drug Safety, 2003.
26. Wu, S., J. Hu, and D. Wildemeersch, *Performance of the frameless GyneFix and the TCu380A IUDs in a 3-year multicenter, randomized, comparative trial in parous women*. Contraception, 2000. 61(2): p. 91-98.
27. Kets, H., et al., *The frameless GyneFix intrauterine implant: A major improvement in efficacy, expulsion and tolerance*. Advances in Contraception, 1995. 11(2): p. 131-142.
28. Cao, X., et al., *Three-year efficacy and acceptability of the GyneFix 200 intrauterine system*. Contraception, 2004. 69(3): p. 201-2011.
29. Wildemeersch, D., et al., *The 'frameless' intrauterine system for long-term, reversible contraception: A review of 15 years of clinical experience*. Journal of Obstetrics and Gynaecology Research, 2003. 29(3): p. 164-173.
30. Meirik, O., et al., *The frameless copper IUD (GyneFix) and the TCu380A IUD: results of an 8-year multicenter randomized comparative trial*. Contraception, 2009. 80(2): p. 133-141.
31. Vekemans, M. and A. Verougstraete, *Late uterine perforation with an anchored IUD, the Gynefix: a case report*. Contraception, 1999. 61(1): p. 55-56.

32. Wildemeersch, D., et al., *GyneFIX. The frameless intrauterine contraceptive implant-an update for interval, emergency and postabortal contraception*. British Journal of Family Planning, 1999. 24(4): p. 149-159.
33. Martinez, F., et al., *Experience with GyneFIX insertions in Spain: favorable acceptance of the intrauterine contraceptive implant with some limitations*. Contraception, 2002. 66(5): p. 315-320.
34. Rosenberg, M., et al., *Performance of the TCu380A and Cu-Fix IUDs in an international randomized trial*. Contraception, 1996. 53: p. 197-203.
35. UNDP, UNFPA, and W.S.P.o.R.D.a.R.T.i.H. Repoduction, *IUD Research Group. The TCu380A IUD and the frameless IUD "The FlexiGard," Interim three-year data from an international multicenter trial*. Contraception, 1995. 52: p. 77-83.
36. Tatum, H., *Intrauterine contraceptives 1972-1993*. Fertility Control, 1994.
37. Wildemeersch, D., *New frameless and framed intrauterine devices and systems—An overview*. Contraception, 2007. 75(6): p. S82-S92.
38. Trussell, J., *The cost of unintended pregnancy in the United States*. Contraception, 2007. 75(3): p. 168-170.
39. Affair, D.o.E.a.S., *Trends in Contraceptive Use Worldwide* 2015. Economic & Social Affairs, 2015.
40. Sonfield, A., *Popularity Disparity: Attitudes About the IUD in Europe and the United States*. Guttmacher Policy Review, Guttmacher, 2007.
41. Buhling, K., N. Zite, and K. Black, *Worldwide use of intrauterine contraception: a review*. Contraception, 2014. 89(3): p. 162-173.
42. Andersson, K., et al., *Perforations with intrauterine devices: Report from a Swedish survey*. Contraception, 1998. 57(4): p. 251-255.
43. Heartwell, S. and S. Schlesseman, Risk of uterine perforations among users of intrauterine devices. Obstet Gynecol, 1983. 25((suppl)): p. 1-11.

The invention claimed is:

1. A system for inserting and securing an intrauterine device in a uterine cavity, the system comprising:
   a barbed suture;
   an intrauterine device configured to couple to the barbed suture; and
   a needle, wherein:
   the needle is configured to direct the barbed suture into a uterine cavity wall;
   the barbed suture comprises a first end and a second end;
   the barbed suture is configured to be removed from the uterine cavity wall when the first end of the barbed suture is pulled in a direction away from the uterine cavity wall; and
   the barbed suture is configured to remain in the uterine cavity wall when the second end of the barbed suture is pulled in a direction away from the uterine cavity wall.

2. The system of claim 1 further comprising a suction device configured to create a vacuum on a target region of the uterine cavity wall.

3. The system of claim 2 wherein the suction device comprises a first end, a second end, an inner conduit, and a plunger disposed within the inner conduit.

4. The system of claim 3 wherein the suction device comprises a first channel configured to guide the needle and the barbed suture toward the uterine cavity wall.

5. The system of claim 4 wherein the suction device comprises a second channel configured to guide the needle and the barbed suture away from the uterine cavity wall.

6. The system of claim 4 wherein the first channel comprises a first curved portion proximal to the first end, wherein the curved portion is configured to direct the needle and the barbed suture toward the inner conduit.

7. The system of claim 6 wherein the second channel comprises a second curved portion configured to direct the needle and the barbed sutured from the inner conduit toward the second end of the suction device.

8. The system of claim 7 wherein:
   the first curved portion is configured to direct the needle to penetrate into the uterine cavity wall at a first location; and
   the second curved portion is configured receive the needle from the uterine cavity wall at a second location.

9. The system of claim 1 wherein the needle is flexible.

10. The system of claim 1 wherein the intrauterine device is a frameless intrauterine device.

11. The system of claim 1 wherein the intrauterine device comprises an aperture configured to receive the barbed suture.

12. The system of claim 1 wherein the barbed suture is biodegradable.

13. The system of claim 12 wherein the barbed suture is configured to degrade and release the intrauterine device in a period of time between one month and one year after the barbed suture is coupled to the intrauterine device and inserted in a uterine cavity wall.

14. The system of claim 12 wherein the barbed suture is configured to degrade and release the intrauterine device in a period of time between six weeks and six months after the barbed suture is coupled to the intrauterine device and inserted in a uterine cavity wall.

15. A method of inserting an intrauterine device in a uterine cavity, the method comprising:
   coupling an intrauterine device to a barbed suture; and
   inserting the barbed suture into a uterine cavity wall to secure the intrauterine device in the uterine cavity, wherein inserting the barbed suture into the uterine wall comprises;
   directing the barbed suture into a first location of the uterine cavity wall; and
   directing the barbed suture out of a second location of the uterine cavity wall.

16. The method of claim 15 further comprising creating a vacuum on a target region of the uterine wall cavity comprising the first location and the second location of the uterine cavity wall.

17. The method of claim 16 wherein creating a vacuum on the target region of the uterine cavity wall comprises:
   placing a suction device proximal to the target region of the uterine cavity wall, wherein the suction device comprises a first end, a second end, an inner conduit, and a plunger disposed within the inner conduit;
   engaging the first end of the suction device with the uterine cavity wall;
   positioning the first end of the suction device around the target region of the uterine cavity wall; and
   moving the plunger away from the first end of the suction device and toward the second end of the suction device.

18. The method of claim 15 wherein the uterine cavity wall is a fundus.

19. The method of claim 15 further comprising positioning the barbed suture such that the barbed suture forms a loop in the uterine cavity.

20. The method of claim 19 wherein the barbed suture comprises a first end and a second end, and wherein the first end and the second end are distal from the uterine cavity wall.

21. The method of claim 20 further comprising removing the barbed suture from the uterine cavity wall by pulling the first end of the barbed suture in a direction away from the uterine cavity wall.

22. The method of claim 15 wherein the barbed suture is biodegradable.

23. The method of claim 22 wherein the barbed suture degrades and releases the intrauterine device in a period of time between one month and one year after the barbed suture is coupled to the intrauterine device and inserted in a uterine cavity wall.

24. The method of claim 22 wherein the barbed suture degrades and releases the intrauterine device in a period of time between six weeks and six months after the barbed suture is coupled to the intrauterine device and inserted in a uterine cavity wall.

* * * * *